US011458363B2

(12) United States Patent
Powers et al.

(10) Patent No.: US 11,458,363 B2
(45) Date of Patent: Oct. 4, 2022

(54) SYSTEM AND METHOD FOR INTELLIGENT SELF-CALIBRATION OF TARGET LOAD THRESHOLDS FOR USERS OF EXERCISE MACHINES

(71) Applicant: Rehab2Fit Technologies, Inc., Longmont, CO (US)

(72) Inventors: Philip Powers, Denver, CO (US); Colin James Smith, Boulder, CO (US); Eric Mundt, Highlands Ranch, CO (US)

(73) Assignee: Rehab2Fit Technologies, Inc., Longmont, CO (US)

( * ) Notice: Subject to any disclaimer, the term of this patent is extended or adjusted under 35 U.S.C. 154(b) by 196 days.

(21) Appl. No.: 16/903,121

(22) Filed: Jun. 16, 2020

(65) Prior Publication Data

US 2020/0391080 A1    Dec. 17, 2020

Related U.S. Application Data

(60) Provisional application No. 62/862,512, filed on Jun. 17, 2019.

(51) Int. Cl.
*A63B 24/00*    (2006.01)
*A61B 6/00*     (2006.01)
(Continued)

(52) U.S. Cl.
CPC .......... *A63B 24/0075* (2013.01); *A61B 6/505* (2013.01); *A63B 23/0405* (2013.01);
(Continued)

(58) Field of Classification Search
CPC ............ A63B 24/0075; A63B 23/0405; A63B 23/1209; A63B 2220/20; A63B 2220/50;
(Continued)

(56) References Cited

U.S. PATENT DOCUMENTS 10,173,094 B2    1/2019    Gomberg et al.
10,173,095 B2    1/2019    Gomberg et al.
(Continued)

OTHER PUBLICATIONS

U.S. Appl. No. 16/812,462, filed Mar. 9, 2020, and titled "System, Method and Apparatus for Adjustable Pedal Crank", by Peter Am, et al.

(Continued)

*Primary Examiner* — Sundhara M Ganesan
(74) *Attorney, Agent, or Firm* — Dickinson Wright, PLLC; Stephen A. Mason; Jonathan H. Harder

(57) ABSTRACT

A system and method for intelligent self-calibration of target load thresholds for users of exercise machines is disclosed herein. In one embodiment, a method includes determining, by one or more processing devices, a bone geometry of a bone in a portion of a body of a user, where said portion is going to be exercised by the user performing an exercise on an exercise machine. The method also includes determining, using the bone geometry, a strain on the bone in the portion of the body of the user such that the strain triggers osteogenesis, determining a target load threshold to be added by the user to the exercise machine during the exercise to achieve the strain that triggers osteogenesis, and, while the user performs the exercise on the exercise machine, causing the target load threshold to be represented on a user interface of a computing device.

20 Claims, 24 Drawing Sheets

(51) Int. Cl.
*A63B 23/04* (2006.01)
*A63B 23/12* (2006.01)
*G16H 20/30* (2018.01)
*G06N 20/00* (2019.01)
*G16H 50/50* (2018.01)

(52) U.S. Cl.
CPC ......... *A63B 23/1209* (2013.01); *G06N 20/00* (2019.01); *G16H 20/30* (2018.01); *G16H 50/50* (2018.01); *A63B 2220/20* (2013.01); *A63B 2220/50* (2013.01); *A63B 2230/01* (2013.01); *A63B 2230/70* (2013.01)

(58) Field of Classification Search
CPC ............ A63B 2230/01; A63B 2230/70; A63B 21/0023; A63B 21/4029; A63B 21/4034; A63B 21/4035; A63B 21/4045; A63B 21/4049; A63B 24/0062; A63B 24/0087; A63B 71/0622; A63B 2024/0068; A63B 2071/0625; A63B 2071/065; A63B 2071/0655; A63B 2208/0204; A63B 2208/0233; A63B 2220/51; A63B 2225/09; A63B 2225/093; A63B 2225/10; A63B 2024/0093; A63B 2225/20; A63B 2225/50; A63B 2230/085; A61B 6/505; A61B 6/5217; G06N 20/00; G16H 20/30; G16H 50/50

See application file for complete search history.

(56) References Cited

U.S. PATENT DOCUMENTS

| | | | |
|---|---|---|---|
| 10,173,096 B2 | 1/2019 | Gomberg et al. | |
| 10,173,097 B2 | 1/2019 | Gomberg et al. | |
| 10,226,663 B2 | 3/2019 | Gomberg et al. | |
| 10,646,746 B1* | 5/2020 | Gomberg | A63B 23/0476 |
| 2004/0067833 A1* | 4/2004 | Talish | A63B 22/0076 |
| | | | 482/148 |
| 2008/0214971 A1* | 9/2008 | Talish | A63B 22/0012 |
| | | | 601/23 |
| 2017/0333080 A1* | 11/2017 | Roschak | A61B 17/68 |
| 2019/0150835 A1* | 5/2019 | Bae | A61B 5/0031 |
| 2020/0391080 A1* | 12/2020 | Powers | A63B 21/4029 |

OTHER PUBLICATIONS

U.S. Appl. No. 16/813,158, filed Mar. 9, 2020, and titled "System, Method and Apparatus for a Rehabilitation Machine With a Simulated Flywheel", by S. Adam Hacking, et al.

U.S. Appl. No. 16/813,303, filed Mar. 9, 2020, and titled "Control System for a Rehabilitation and Exercise Electromechanical Device", by S. Adam Hacking, et al.

U.S. Appl. No. 16/813,224, filed Mar. 9, 2020, and titled "System, Method and Apparatus for Electrically Actuated Pedal For an Exercise or Rehabilitation Machine", by S. Adam Hacking, et al.

* cited by examiner

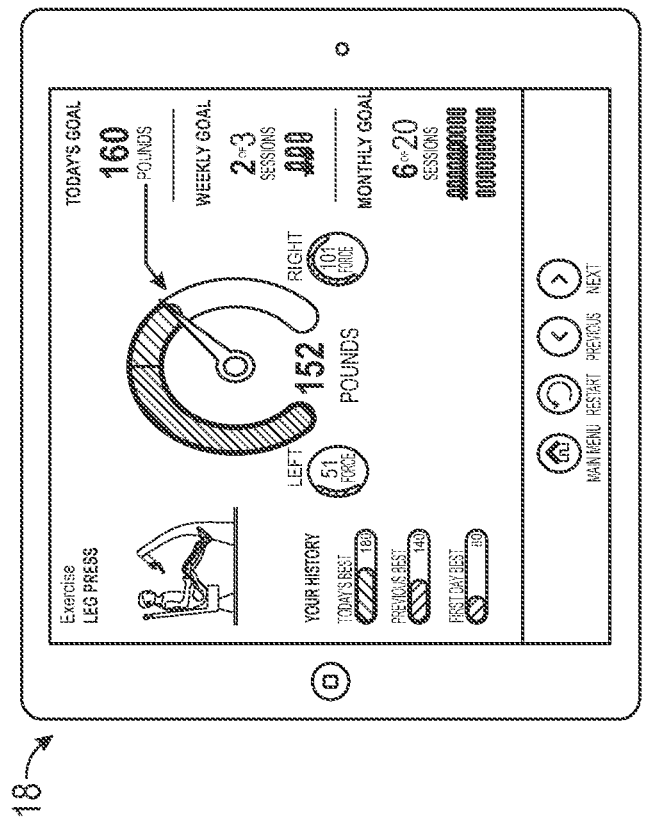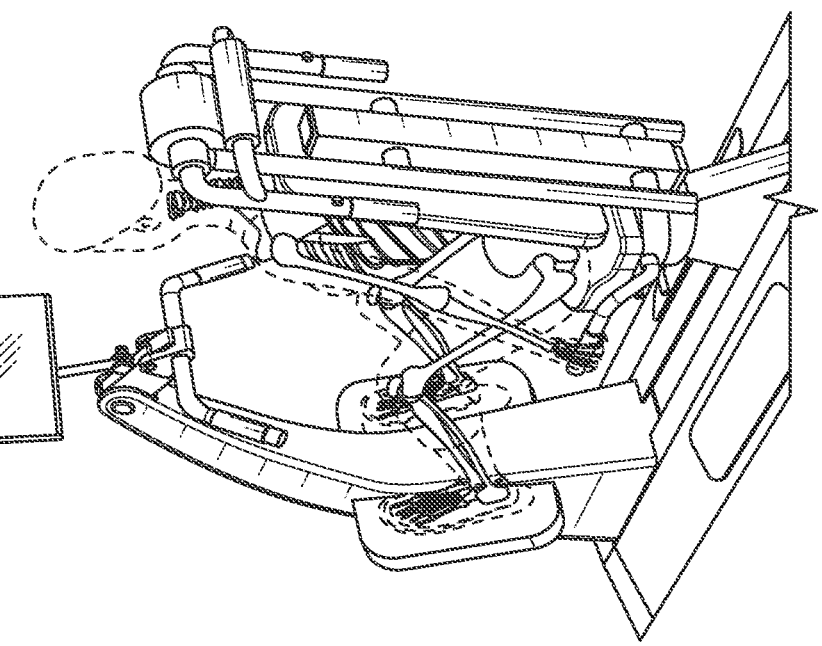
FIG. 13

1906

Determine a target load threshold representing an amount of Load to be added by the user to the exercise machine during the exercise to achieve the Strain that triggers osteogenesis ⸺2200

2202

Simulate, using a physical mathematical model of the bone having the bone geometry, one or more axial Loads on the bone having the bone geometry

2204

Select an axial load as the target load threshold when the axial load causes the strain on the bone in the portion of the body of the user that triggers osteogenesis

Determine a target load threshold representing an amount of load to be added by the user to the exercise machine during the exercise to achieve the strain that triggers osteogenesis ⸺2210

2212

Train a machine learning model to output target load threshold based at least on bone geometry using empirical data

2214

Input the bone geometry of the bone into a machine learning model trained to output the target load threshold based at least on the bone geometry

*FIG. 22B*

SYSTEM AND METHOD FOR INTELLIGENT SELF-CALIBRATION OF TARGET LOAD THRESHOLDS FOR USERS OF EXERCISE MACHINES

CROSS-REFERENCE TO RELATED APPLICATIONS

This application claims priority to and the benefit of U.S. Provisional Application Patent Ser. No. 62/862,512 filed Jun. 17, 2019, the entire disclosure of which is hereby incorporated by reference.

TECHNICAL FIELD

This disclosure relates to exercise machines. More specifically, this disclosure relates to a system and method for intelligent self-calibration of target load thresholds for users of exercise machines.

BACKGROUND

Osteogenic isometric exercise and/or rehabilitation and/or strength training equipment is used to facilitate isometric exercises. A user may perform an exercise (e.g., bench press, pull down, arm curl, etc.) using the osteogenic isometric exercise and/or rehabilitation and/or strength training equipment to improve osteogenesis, bone growth, bone density, muscular hypertrophy, muscular strength, or some combination thereof. The isometric exercise and/or rehabilitation and/or strength training equipment may include non-movable portions onto which the user adds load. For example, to perform a leg-press-style exercise, the user may sit in a seat, place each of their feet on a respective foot plate, and push on the feet plate with their feet while the feet plate remain in the same position.

SUMMARY

Representative embodiments set forth herein disclose various techniques for enabling a system and method for improving completion of an exercise using an exercise machine. As used herein, the term "exercise machine" and "isometric exercise and rehabilitation assembly" may be used interchangeably. The term "exercise machine" and the term "isometric exercise and rehabilitation assembly" may also refer to an osteogenic, strength training, isometric exercise, and/or rehabilitation assembly.

In one embodiment, a method includes determining, by one or more processing devices, a bone geometry of a bone in a portion of a body of a user, such that the portion is going to be exercised by the user performing an exercise on an exercise machine. The method also includes determining, using the bone geometry, a strain on the bone in the portion of the body of the user, wherein the strain is needed to trigger osteogenesis, determining a target load threshold representing an amount of load to be added by the user to the exercise machine during the exercise to achieve the strain that triggers osteogenesis, and while the user performs the exercise on the exercise machine, causing the target load threshold to be represented on a user interface of a computing device.

In one embodiment, a tangible, non-transitory computer-readable medium is disclosed. The computer-readable medium store instructions that, when executed by a processing device, cause the processing device to determine a bone geometry of a bone in a portion of a body of a user, such that the portion is going to be exercised by the user performing an exercise on an exercise machine, determine, using the bone geometry, a strain on the bone in the portion of the body of the user, wherein the strain is needed to trigger osteogenesis, determine a target load threshold representing an amount of load to be added by the user to the exercise machine during the exercise to achieve the strain that triggers osteogenesis, and while the user performs the exercise on the exercise machine, cause the target load threshold to be represented on a user interface of a computing device.

In one embodiment, a system includes one or more memory devices storing instructions and one or more processing devices communicatively coupled to the one or more memory devices. The one or more processing devices are configured to execute the instructions to determine a bone geometry of a bone in a portion of a body of a user, such that the portion is going to be exercised by the user performing an exercise on an exercise machine, determine, using the bone geometry, a strain on the bone in the portion of the body of the user, wherein the strain is needed to trigger osteogenesis, determine a target load threshold representing an amount of load to be added by the user to the exercise machine during the exercise to achieve the strain that triggers osteogenesis, and while the user performs the exercise on the exercise machine, cause the target load threshold to be represented on a user interface of a computing device.

Other technical features may be readily apparent to one skilled in the art from the following figures, descriptions, and claims.

BRIEF DESCRIPTION OF THE DRAWINGS

For a detailed description of example embodiments, reference will now be made to the accompanying drawings in which:

FIG. 13 illustrates a side view of the second embodiment of the isometric exercise and rehabilitation assembly with a user performing a leg-press-style exercise and a user interface presenting information to the user;

FIGS. 22A-22B illustrate example operations of methods for determining a target load threshold to be added by the user to the exercise machine during the exercise to achieve the strain that triggers osteogenesis;

NOTATION AND NOMENCLATURE

Figure 1:
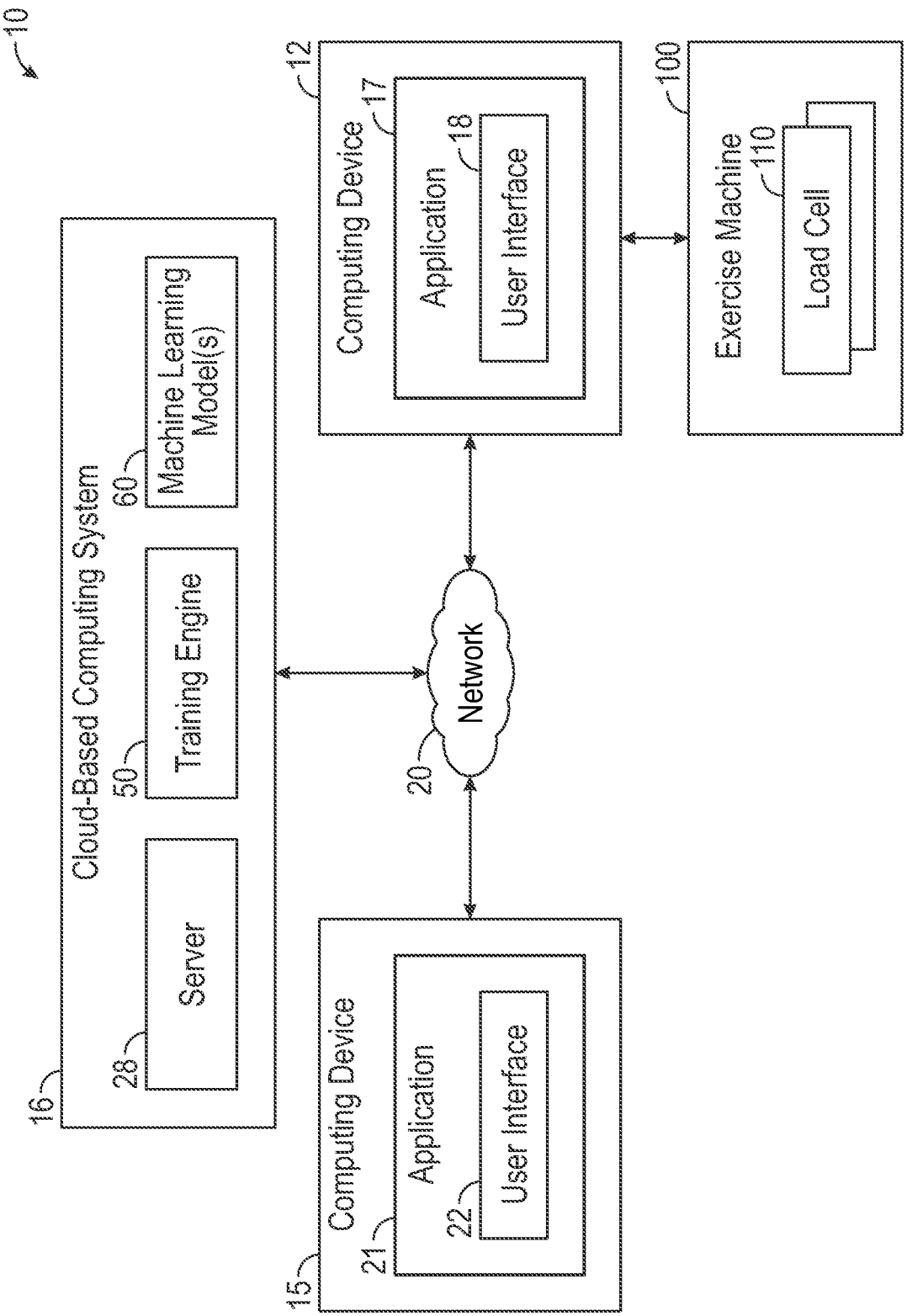
FIG. 1 illustrates a high-level component diagram of an illustrative system architecture according to certain embodiments of this disclosure.
Figure 2:
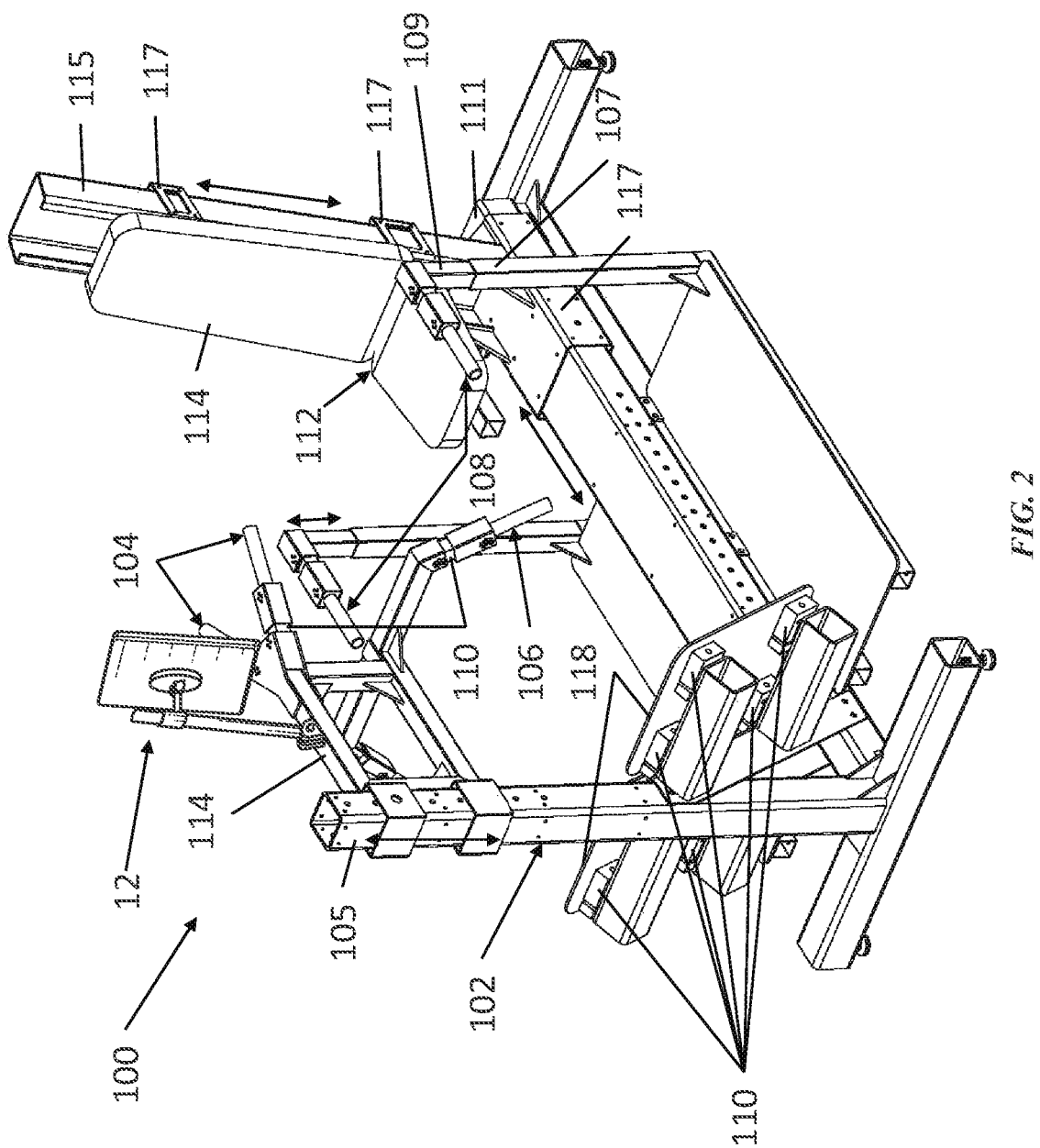
FIG. 2 illustrates an elevated perspective view of one embodiment of an isometric exercise and rehabilitation assembly.
Figure 3:
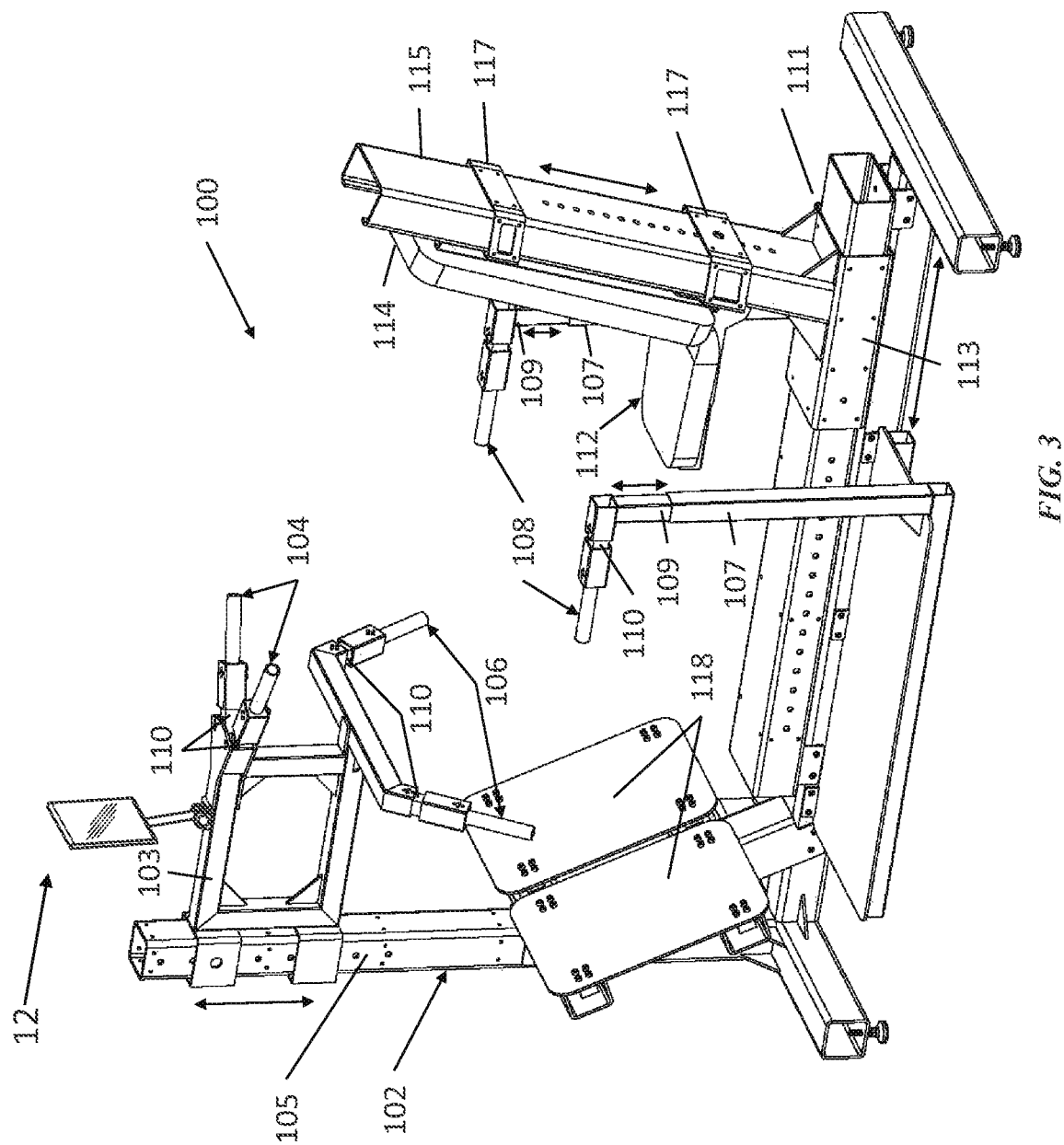
FIG. 3 illustrates a perspective view of the isometric exercise and rehabilitation assembly.
Figure 4:
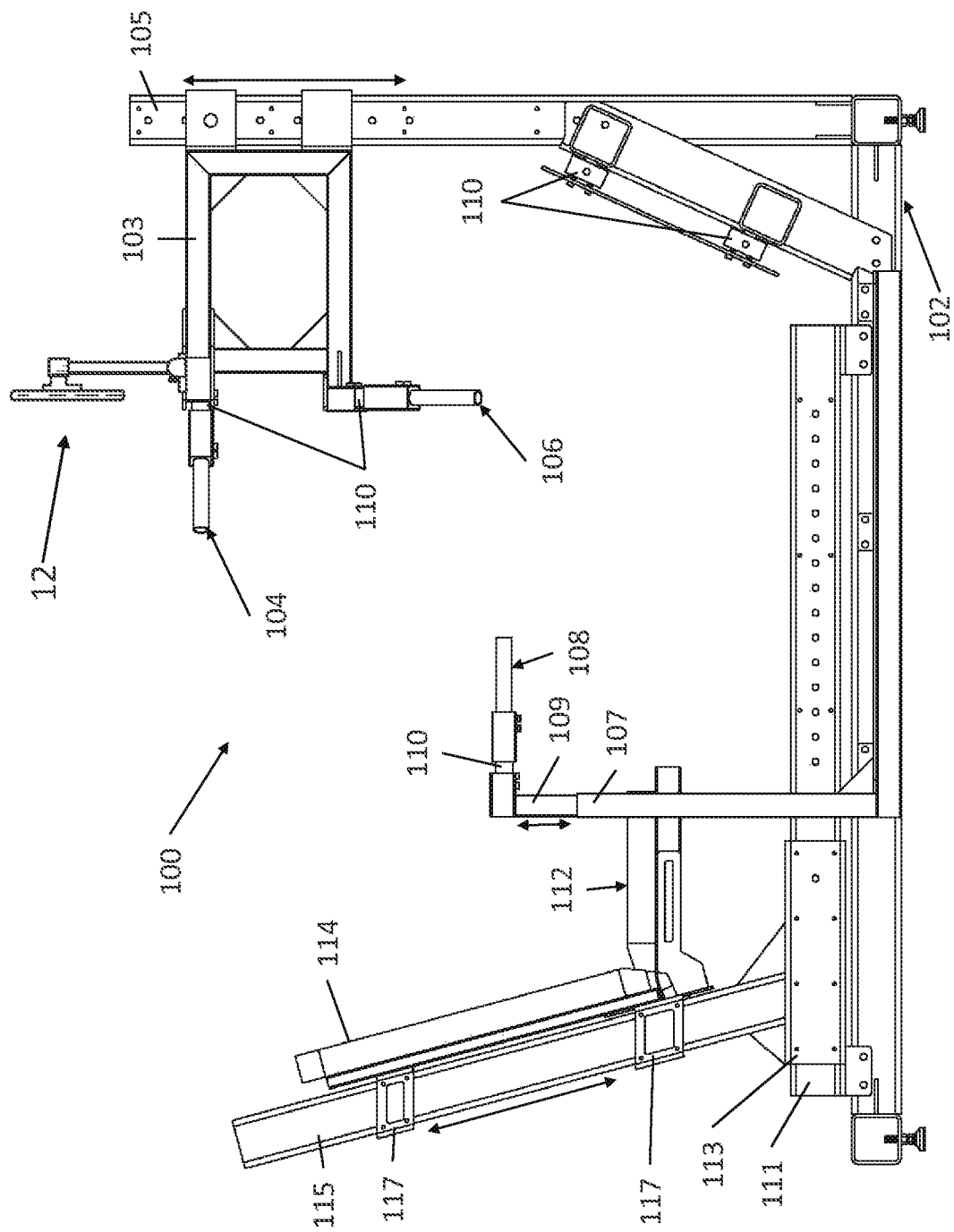
FIG. 4 illustrates a side view of the isometric exercise and rehabilitation assembly.
Figure 5:
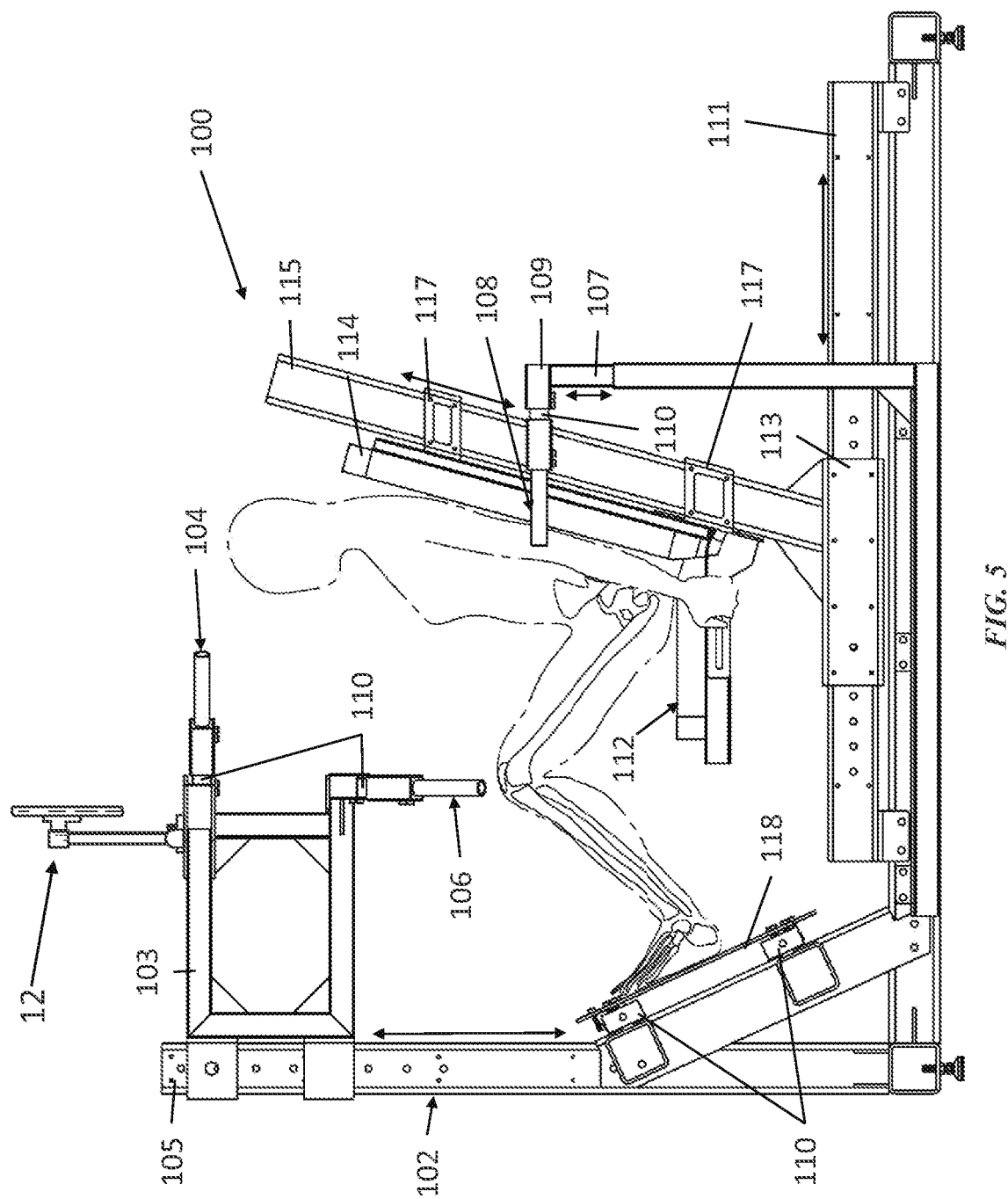
FIG. 5 illustrates a side view of the isometric exercise and rehabilitation assembly with a user performing a leg-press-style exercise.
Figure 6:
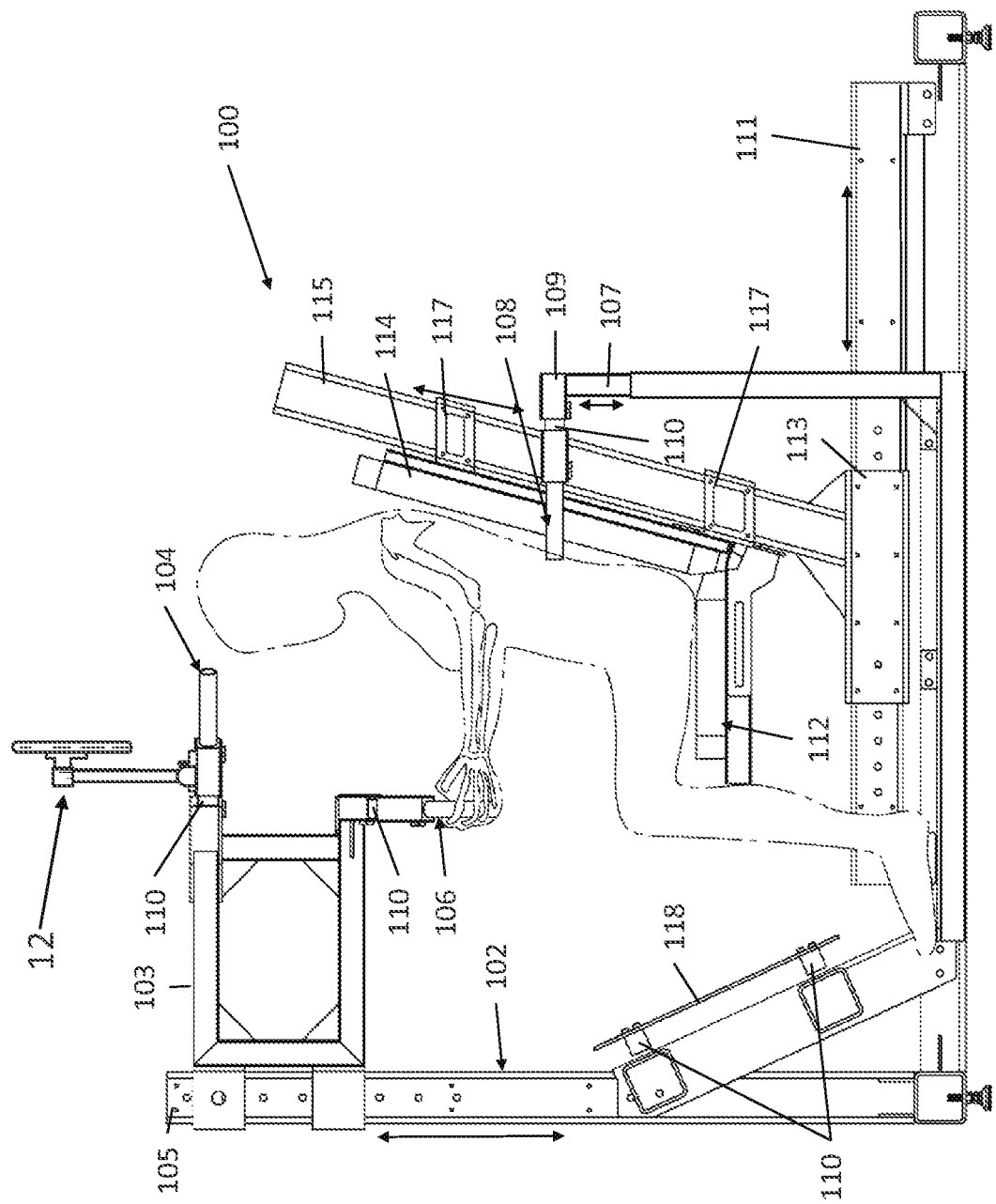
FIG. 6 illustrates a side view of the isometric exercise and rehabilitation assembly with a user performing a chest-press-style exercise.
Figure 7:
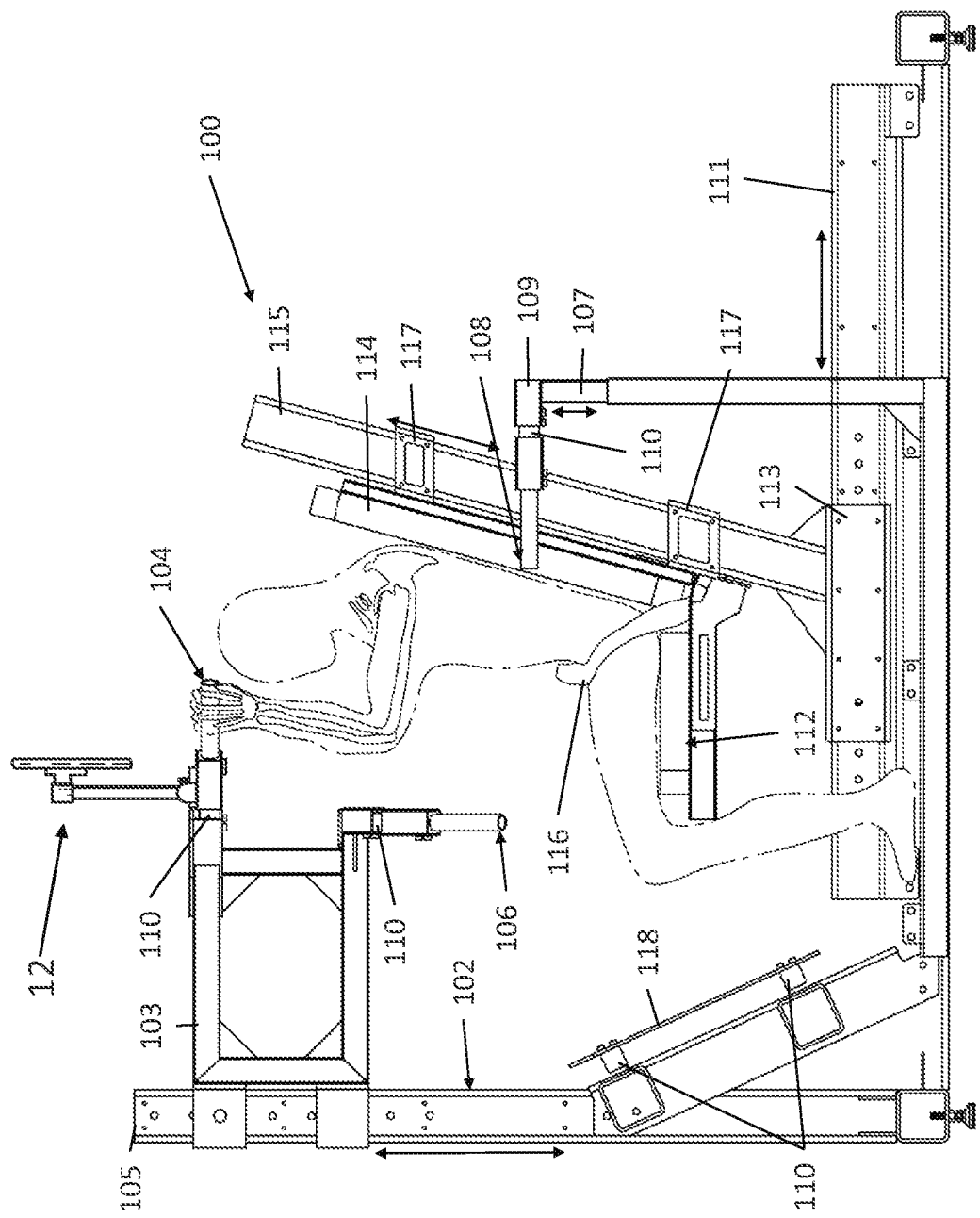
FIG. 7 illustrates a side view of the isometric exercise and rehabilitation assembly with a user performing a core-pull-style exercise.
Figure 8:
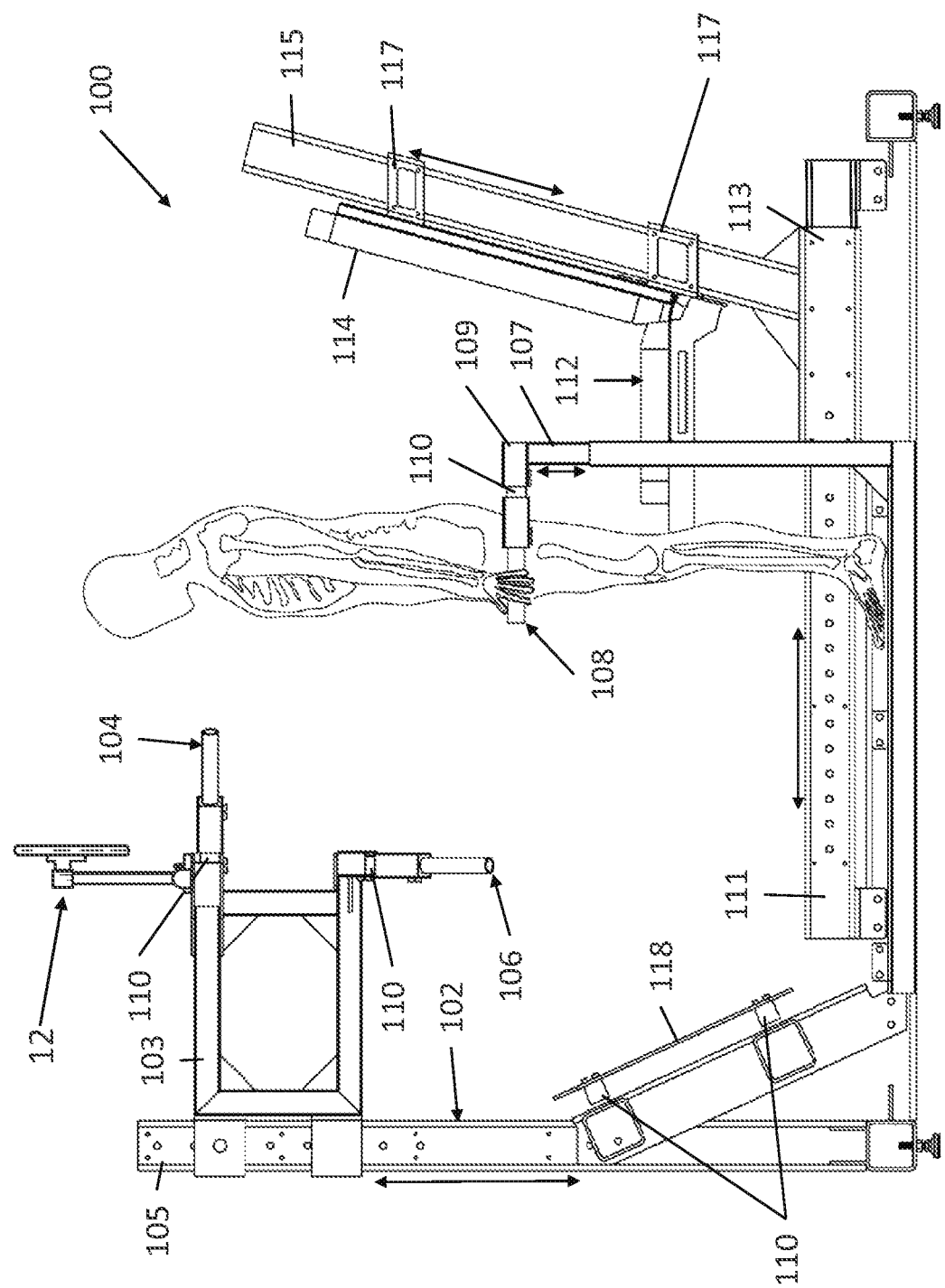
FIG. 8 illustrates a side view of the isometric exercise and rehabilitation assembly with a user performing a suitcase-lift-style exercise.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drives (SSDs), flash memory, or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

The term "bone geometry" may refer to bone diameter, bone density, bone shape, bone cross-section, bone length, bone weight, or any suitable bone dimension(s) and/or measurement(s).

The term "empirical data" may refer to data obtained and/or derived based on observation, experience, measurement, and/or research.

The term "strain," when used in context with a bone of a user, may refer to an amount, proportion, or degree of deformation of the bone material.

The terms "exercise machine" and "isometric exercise and rehabilitation assembly" may be used interchangeably herein.

Definitions for other certain words and phrases are provided throughout this patent document. Those of ordinary skill in the art should understand that in many if not most instances, such definitions apply to prior as well as future uses of such defined words and phrases.

DETAILED DESCRIPTION

Conventional exercise machines, such as those promoting osteogenesis, do not tailor target load thresholds to individual users. There is typically an arbitrary, preset load threshold used for the users. The conventional target load thresholds may cause users to perform inefficient workouts by meeting target load thresholds insufficient to trigger osteogenesis. Further, the target load thresholds do not dynamically adjust as the bones grow over time.

To enhance osteogenesis, the isometric exercise and rehabilitation equipment of the disclosure may separately measure forces exerted by both the left and right sides of the user, thereby enabling bone growth. Some embodiments may, based on an initial bone geometry and ongoing bone geometries of the user in view of empirical data related to bone geometries of people and corresponding loads that cause strains on the bones that trigger osteogenesis, determine initial and ongoing target load thresholds for triggering osteogenesis for a user using an exercise machine. The disclosed techniques determine target load thresholds tailored to the user based on at least individualized data, such as bone geometries measured and/or inferred, initially and over time. As the bone geometries of the users change over time (e.g., bone density grows), the target load thresholds may adjust to values that trigger osteogenesis for those bone geometries. By using individualized data and/or empirical data, target load thresholds tailored for each specific user to cause automatic self-calibration of target load thresholds for the user may be determined. Each user may exercise and attempt to exceed these target load thresholds tailored for them, and as a result, may experience greater osteogenesis. The disclosed techniques may improve a user experience with the exercise machine and/or using a computing device of the exercise machine by providing the user with the tailored target load thresholds and congratulated or otherwise rewarding the user or reinforcing the user's behavior when the target load thresholds are exceeded.

Osteogenesis

As typically healthy people grow from infants to children to adults, they experience bone growth. Such, growth, however, typically stops at approximately age 30. After that point, without interventions as described herein, bone loss (called osteoporosis), can start to occur. This does not mean that the body stops creating new bone. Rather, it means that the rate at which it creates new bone tends to slow, while the rate at which bone loss occurs tends to increase.

In addition, as people age and/or become less active than they once were, they may experience muscle loss. For example, muscles that are not used often may reduce in muscle mass. As a result, the muscles become weaker. In some instances, people may be affected by a disease, such as muscular dystrophy, that causes the muscles to become progressively weaker and to have reduced muscle mass. To increase the muscle mass and/or reduce the rate of muscle loss, people may exercise a muscle to cause muscular hypertrophy, thereby strengthening the muscle as the muscle grows. Muscular hypertrophy may refer to an increase in a size of skeletal muscle through a growth in size of its component cells. There are two factors that contribute to muscular hypertrophy, (i) sarcoplasmic hypertrophy (increase in muscle glycogen storage), and (ii) myofibrillar hypertrophy (increase in myofibril size). The growth in the cells may be caused by an adaptive response that serves to increase an ability to generate force or resist fatigue.

The rate at which such bone or muscle loss occurs generally accelerates as people age. A net growth in bone can ultimately become a net loss in bone, longitudinally across time. In an average case, but noting that significant individual variations in age do occur, by the time women are over 50 and men are over 70, net bone loss can reach a point where brittleness of the bones is so great that an increased risk of life-altering fractures can occur. Examples of such fractures include fractures of the hip and femur. Of course, fractures can also occur due to participation in athletics or due to accidents. In such cases, it is just as relevant to have a need for bone growth which heals or speeds the healing of the fracture.

To understand why such fractures occur, it is useful to recognize that bone is itself porous, with a somewhat-honeycomb like structure. This structure may be dense and therefore stronger or it may be variegated, spread out and/or sparse, such latter structure being incapable of continuously or continually supporting the weight (load) stresses experienced in everyday living. When such loads exceed the support capability of the structure at a stressor point or points, a fracture occurs. This is true whether the individual had a fragile bone structure or a strong one: it is a matter of physics, of the literal "breaking point."

It is therefore preferable to have a means of mitigating or ameliorating bone loss and of healing fractures; and, further, of encouraging new bone growth, thus increasing the density of the structure described hereinabove, thus increasing the load-bearing capacities of same, thus making first or subsequent fractures less likely to occur, and thus improving the individual's quality of life. The process of bone growth itself is referred to as osteogenesis, literally the creation of bone.

It is also preferable to have a means for mitigating or ameliorating muscle mass loss and weakening of the muscles. Further, it is preferable to encourage muscle growth by increasing the muscle mass through exercise. The increased muscle mass may enable a person to exert more force with the muscle and/or to resist fatigue in the muscle for a longer period of time.

In order to create new bone, at least three factors are necessary. First, the individual must have a sufficient intake of calcium, but second, in order to absorb that calcium, the individual must have a sufficient intake and absorption of Vitamin D, a matter problematic for those who have cystic fibrosis, who have undergone gastric bypass surgery or have other absorption disorders or conditions which limit absorption. Separately, supplemental estrogen for women and supplemental testosterone for men can further ameliorate bone loss. On the other hand, abuse of alcohol and smoking can harm one's bone structure. Medical conditions such as, without limitation, rheumatoid arthritis, renal disease, overactive parathyroid glands, diabetes or organ transplants can also exacerbate osteoporosis. Ethical pharmaceuticals such as, without limitation, hormone blockers, seizure medications and glucocorticoids are also capable of inducing such exacerbations. But even in the absence of medical conditions as described hereinabove, Vitamin D and calcium taken together may not create osteogenesis to the degree necessary or possible; or ameliorate bone loss to the degree necessary or possible.

To achieve such a degree of osteogenesis, therefore, one must add in the third factor: exercise. Specifically, one must subject one's bones to a force at least equal to certain multiple of body weight, such multiples varying depending on the individual and the specific bone in question. As used herein, "MOB" means Multiples of Body Weight. It has been determined through research that subjecting a given bone to a certain threshold MOB (this may also be known as a "weight-bearing exercise"), even for an extremely short period of time, one simply sufficient to exceed the threshold MOB, encourages and fosters osteogenesis in that bone.

Further, a person can achieve muscular hypertrophy by exercising the muscles for which increased muscle mass is desired. Strength training and/or resistance exercise may cause muscle tissue to increase. For example, pushing against or pulling on a stationary object with a certain amount of force may trigger the cells in the associated muscle to change and cause the muscle mass to increase.

The subject matter disclosed herein relates to a machine and methods and apparatuses appurtenant thereto, not only capable of enabling an individual, preferably an older, less mobile individual or preferably an individual recovering from a fracture, to engage easily in osteogenic exercises, but capable of using self-calibrating target load thresholds, such that the person using the machine can be immediately informed through visual and/or other sensorial feedback, that the osteogenic threshold has been exceeded, thus triggering osteogenesis for the subject bone (or bones) and further indicating that the then-present exercise may be terminated, enabling the person to move to a next machine-enabled exercise to enable osteogenesis in a preferably different bone or bones.

For those with any or all of the osteoporosis-exacerbating medical conditions described herein, such a machine can slow the rate of net bone loss by enabling osteogenesis to occur without exertions which would not be possible for someone whose health is fragile, not robust. Another benefit of the disclosed techniques, therefore, is enhancing a rate of healing of fractures in athletically robust individuals.

Last, while this discussion has focused purely on osteogenesis, an additional benefit is that partaking in exercises which focus on osteogenesis may, in certain embodiments, also increase muscle strength and, as a physiological system, musculoskeletal strength.

Hypertrophy

Hypertrophy is defined as an increase in volume or bulk of a tissue or organ produced entirely by enlargement of existing cells. Hypertrophy as described herein specifically refers to muscle hypertrophy. The exercises performed using the disclosed apparatus may involve the following types of muscle contractions: concentric contractions (shorten), eccentric contractions (lengthen), and isometric contractions (remain the same).

Bone Exercises and their Benefits

The following exercises achieve bone strengthening results by exposing relevant parts of a user to isometric forces which are selected multiples of body weight (MOB) of the user, a threshold level above which bone mineral density increases. The specific MOB-multiple threshold necessary to effect such increases will naturally vary from individual to individual and may be more or less for any given individual. "Bone-strengthening," as used herein, specifically includes, without limitation, a process of osteogenesis, whether due to the creation of new bone as a result of an increase in the bone mineral density; or proximately to the introduction or causation of microfractures in the underlying bone. The exercises referred to are as follows.

Leg Press

An isometric leg-press-style exercise to improve muscular strength in the following key muscle groups: gluteals, hamstrings, quadriceps, spinal extensors and grip muscles, as well as to increase resistance to skeletal fractures in leg bones such as the femur. In one example, the leg-press-style exercise can be performed at approximately 4.2 MOB or more of the user.

Chest Press

An isometric chest-press-style exercise to improve muscular strength in the following key muscle groups: pectorals, deltoids, and tricep and grip muscles, as well as to increase resistance to skeletal fractures in the humerus, clavicle, radial, ulnar and rib pectoral regions. In one example, the chest-press-style exercise can be performed at approximately 2.5 MOB or more of the user.

Suitcase Lift

An isometric suitcase-lift-style exercise to improve muscular strength in the following key muscle groups: gluteals, hamstrings, quadriceps, spinal extensors, abdominals, and upper back and grip muscles, as well as to increase resistance to skeletal fractures in the femur and spine. In one example, the suitcase-lift-style exercise can be performed at approximately 2.5 MOB or more of the user.

Arm Curl

An isometric arm-curl-style exercise to improve muscular strength in the following key muscle groups: biceps, brachialis, brachioradialis, grip muscles and trunk, as well as to increase resistance to skeletal fractures in the humerus, ribs and spine. In one example, the arm-curl-style exercise can be performed at approximately 1.5 MOB or more of the user.

Core Pull

An isometric core-pull-style exercise to improve muscular strength in the following key muscle groups: elbow flexors, grip muscles, latissimus dorsi, hip flexors and trunk, as well as to increase resistance to skeletal fractures in the ribs and spine. In one example, the core-pull-style exercise can be performed at approximately 1.5 MOB or more of the user.

Grip Strength

A grip-strengthening-style exercise which may preferably be situated around, or integrated with, a station in an exercise machine, in order to improve strength in the muscles of the hand, forearm, or other gripping extremity. Moreover, measurement of grip strength can be taken prior to, during, and/or after the grip-strengthening-style exercise is performed. Grip strength is medically salient because it has been positively correlated with a better state of health. Accordingly, measurements of grip strength can be used to in conjunction with and/or to guide, assist, or enhance the exercise and rehabilitation of a user. Furthermore, a measurement of grip strength during the grip-strengthening-style exercise can be used to provide real-time-feedback to the user. Such real-time-feedback during the grip-strengthening-style exercise can be used to challenge the user to increase a grip strength to further strengthen the muscles of the hand, forearm, or other gripping extremity.

In the following description, details are set forth to facilitate an understanding of the present disclosure. In some instances, certain structures and techniques have not been described or shown in detail in order not to obscure the disclosure.

The following discussion is directed to various embodiments of the present disclosure. Although these embodiments are given as examples, the embodiments disclosed should not be interpreted, or otherwise used, as limiting the scope of the disclosure, including the claims. In addition, one of ordinary skill in the art will understand that the following description has broad application. The discussion of any embodiment is meant only to be exemplary of that embodiment. Thus, the discussion is not intended to intimate that the scope of the disclosure, including the claims, is limited to that embodiment.

Exercise machines can provide isometric exercises to facilitate osteogenesis and muscle hypertrophy. Such exercise machines can include equipment in which there are no moving parts while the user is performing an isometric exercise. While there may be some flexing: (i) under load, (ii) incidental movement resulting from the tolerances of interlocking parts, and (iii) parts that can move while a user performs adjustments on the exercise machines, these flexions and movements can comprise, without limitation, exercise machines capable of isometric exercise and rehabilitation. In addition, such exercise machines may also include equipment or devices including moving parts to provide dynamic exercises to facilitate osteogenesis and muscle hypertrophy. A dynamic exercise can be, but is not limited to, an exercise where a user participates in an activity where the user moves and some resistance or load is provided against the movement of the user.

The control system of the exercise machine may determine a bone geometry of a bone in a portion of a user's body to be exercised by the user performing an exercise on the exercise machine. The control system may determine, using the bone geometry, a strain on the bone in the portion of the body of the user to trigger osteogenesis. The control system may also determine one or more target load thresholds, each representing an amount of load to be added by the user to the exercise machine during the exercise in order to achieve the strain triggering osteogenesis. In some embodiments, one or more target load thresholds may be determined (e.g., a left target load threshold for a left side of the body and a right target load threshold for a right side of the body). The control system may cause the target load threshold to be represented on a user interface while the user performs the exercise on the exercise machine.

The control system may receive one or more load measurements associated with forces exerted or loads applied by both the left and right sides on left and right portions (e.g., handles, foot plate or platform) of the exercise machine to enhance osteogenesis, bone growth, bone density improvement, and/or muscle mass. The one or more load measurements may be a left load measurement of a load added to a left load cell on a left portion of the exercise machine and a right load measurement of a load added to a right load cell on a right portion of the exercise machine. The user interface may be provided by the control system that presents visual representations of the separately measured left load and right load when the respective left load and right load are added to the respective left load cell and right load cell at the subject portions of the exercise machine.

The control system may compare the one or more load measurements (e.g., raw load measurements, or averaged load measurements) to the one or more target load thresholds. In some embodiments, a single load measurement may be compared to a single specific target load threshold (e.g., a one-to-one relationship). In some embodiments, a single load measurement may be compared to more than one specific target load threshold (e.g., a one-to-many relationship). In some embodiments, more than one load measurement may be compared to a single specific target load threshold (e.g., a many-to-one relationship). In some embodiments, more than one load measurement may be compared to more than one specific target load threshold (e.g., a many-to-many relationship).

The control system may determine whether the one or more load measurements exceed the one or more target load thresholds. Responsive to determining that the one or more load measurements exceed the one or more target load thresholds, the control system may cause a user interface to present an indication that the one or more target load thresholds have been exceeded and an exercise is complete.

FIG. 1 illustrates a high-level component diagram of an illustrative system architecture 10 according to certain embodiments of this disclosure. In some embodiments, the system architecture 10 may include a computing device 12 communicatively coupled to an exercise machine 100. The computing device 12 may also be communicatively coupled with a computing device 15 and a cloud-based computing system 16. As used herein, a cloud-based computing system refers, without limitation, to any remote or distal computing system accessed over a network link. Each of the computing device 12, computing device 15, and/or the exercise machine 100 may include one or more processing devices, memory devices, and network interface devices. In some embodiments, the computing device 12 may be included as part of the structure of the exercise machine 100. In some embodiments, the computing device 12 may be separate from the exercise machine 100. For example, the computing device 12 may be a smartphone, tablet, laptop, or the like.

The network interface devices may enable communication via a wireless protocol for transmitting data over short distances, such as Bluetooth, ZigBee, near field communication (NFC), etc. In some embodiments, the computing device 12 is communicatively coupled to the exercise machine 100 via Bluetooth. Additionally, the network interface devices may enable communicating data over long distances, and in one example, the computing device 12 may communicate with a network 20. Network 20 may be a public network (e.g., connected to the Internet via wired (Ethernet) or wireless (WiFi)), a private network (e.g., a local area network (LAN), wide area network (WAN), virtual private network (VPN)), or a combination thereof.

The computing device 12 may be any suitable computing device, such as a laptop, tablet, smartphone, or computer. The computing device 12 may include a display that is capable of presenting a user interface 18 of an application 17. The application 17 may be implemented in computer instructions stored on the one or more memory devices of the computing device 12 and executable by the one or more processing devices of the computing device 12. The application 17 may be a stand-alone application that is installed on the computing device 12 or may be an application (e.g., website) that executes via a web browser. The user interface 18 may present various screens to a user that enable the user to login, enter personal information (e.g., health information; age; gender; activity level; bone geometry; weight; height; patient measurements; etc.), view an exercise plan, initiate an exercise in the exercise plan, view visual representations of left load measurements and right load measurements that are received from left load cells and right load cells during the exercise, view a weight in pounds that are pushed, lifted, or pulled during the exercise, view target load measurements that are determined specifically for the user based on at least the bone geometry of the user, view an indication when the user has exceeded the target load thresholds, and so forth, as described in more detail below. The computing device 12 may also include instructions stored on the one or more memory devices that, when executed by the one or more processing devices of the computing device 12, perform operations to control the exercise machine 100.

The computing device 15 may execute an application 21. The application 21 may be implemented in computer instructions stored on the one or more memory devices of the computing device 15 and executable by the one or more processing devices of the computing device 15. The application 21 may present a user interface 22 including various screens to a physician, trainer, or caregiver that enable the person to create an exercise plan for a user based on a treatment (e.g., surgery, medical procedure, etc.) the user underwent and/or injury (e.g., sprain, tear, fracture, etc.) the user suffered, view progress of the user throughout the exercise plan, and/or view measured properties (e.g., force exerted on portions of the exercise machine 100) of the user during exercises of the exercise plan. The exercise plan specific to a patient may be transmitted via the network 20 to the cloud-based computing system 16 for storage and/or to the computing device 12 so the patient may begin the exercise plan. The exercise plan may specify one or more exercises that are available at the exercise machine 100.

The exercise machine 100 may be an osteogenic, muscular strengthening, isometric exercise and/or rehabilitation assembly. Solid state, static, or isometric exercise and rehabilitation equipment (e.g., exercise machine 100) can be used to facilitate osteogenic exercises that are isometric in nature and/or to facilitate muscular strengthening exercises. Such exercise and rehabilitation equipment can include equipment in which there are no moving parts while the user is exercising. While there may be some flexing under load, incidental movement resulting from the tolerances of interlocking parts, and parts that can move while performing adjustments on the exercise and rehabilitation equipment, these flexions and movements can comprise, without limitation, exercise and rehabilitation equipment from the field of isometric exercise and rehabilitation equipment.

The exercise machine 100 may include various load cells 110 disposed at various portions of the exercise machine 100. For example, one or more left load cells 110 may be located at one or more left feet plates or platforms, and one or more right load cells may be located at one or more right feet plates or platforms. Also, one or more left load cells may be located at one or more left handles, and one or more right load cells may be located at one or more right handles. Each exercise in the exercise system may be associated with both a left and a right portion (e.g., handle or foot plate) of the exercise machine 100. For example, a leg-press-style exercise is associated with a left foot plate and a right foot plate. The left load cell at the left foot plate and the right load cell at the right foot plate may independently measure a load added onto the left foot plate and the right foot plate, respectively, and transmit the left load measurement and the right load measurement to the computing device 12. The load added onto the load cells 110 may represent an amount of weight added onto the load cells. In some embodiments, the load added onto the load cells 110 may represent an amount of force exerted by the user on the load cells. Accordingly, the left load measurement and the right load measurement may be used to present a left force (e.g., in Newtons) and a right force (e.g., in Newtons). The left force and right force may be totaled and converted into a total weight in pounds for the exercise. Each of the left force, the right force, and/or the total weight in pounds may be presented on the user interface 18.

In some embodiments, the cloud-based computing system 16 may include one or more servers 28 that form a distributed, grid, and/or peer-to-peer (P2P) computing architecture. Each of the servers 28 may include one or more processing devices, memory devices, data storage, and/or network interface devices. The servers 28 may be in communication with one another via any suitable communication protocol. The servers 28 may store profiles for each of the users that use the exercise device 100. The profiles may include information about the users such as one or more bone geometries of bones over time, exercise plans, a historical performance (e.g., loads applied to the left load cell and right load cell, total weight in pounds, etc.) for each type of exercise that can be performed using the exercise machine 100, health, age, race, credentials for logging into the application 17, and so forth.

In some embodiments, the cloud-based computing system 16 may include a training engine 50 and/or one or more machine learning models 60. The training engine 50 and/or the one or more machine learning models 60 may be communicatively coupled to the servers 28 or may be included in one of the servers 28. In some embodiments, the training engine 50 and/or the machine learning models 60 may be included in the computing device 12.

The one or more of machine learning models 60 may refer to model artifacts created by the training engine 50 using training data that includes training inputs and corresponding target outputs (correct answers for respective training inputs). The training engine 50 may find patterns in the training data that map the training input to the target output (the answer to be predicted), and provide the machine learning models 60 that capture these patterns. As described in more detail below, the set of machine learning models 60 may comprise, e.g., a single level of linear or non-linear operations (e.g., a support vector machine [SVM]) or a deep network, i.e., a machine learning model comprising multiple levels of non-linear operations. Examples of such deep networks are neural networks including, without limitation, convolutional neural networks, recurrent neural networks with one or more hidden layers, and fully connected neural networks.

In some embodiments, the training data may include empirical data of correlated changes of bone geometries of users, where such changes result from strains caused by applications of loads by the users onto the exercise machine as the users perform various exercises. The empirical data may include data related to changes to the bone geometry of the user caused by strains on the bone resulting from the user applying loads while the user is performing the exercise. The empirical data may include one or more baseline multiples of body weights identified through research as causing osteogenesis for various bones of users. The training data may include other data correlated with the empirical data. For example, the training data may include heights of users, weights of users, body mass indices of users, ages of users, health conditions of users, races of users, genders of users, and so forth.

In some embodiments, the training engine 50 may train the machine learning models 60 to output a bone geometry using the training data and based at least on one of a height of the user, a body mass index of the user, or a weight of the user. The machine learning models 60 may receive at least one of the height of the user, the body mass index of the user, and the weight of the user as input and may output the bone geometry.

In some embodiments, using the training data, the training engine 50 may train the machine learning models 60 to output a strain that causes osteogenesis on a bone based at least on the bone geometry. The machine learning models 60 may receive the bone geometry as input and may output the strain.

In some embodiments, the training engine 50 may train the machine learning models 60 to output a target load threshold based at least on the bone geometry using the training data. The machine learning models 60 may receive the bone geometry as input and may output the target load threshold.

In some embodiments, the training engine 50 may train the machine learning models 60 to output a target load threshold based at least on the strain using the training data. The machine learning models 60 may receive the strain as input and may output the target load threshold.

In some embodiments, the machine learning models 60 are linked such that their outputs are used as inputs to one another. For example, the bone geometry output by a first machine learning model 60 may be input into a second machine learning model 60 that outputs the strain. The strain output by the second machine learning model 60 may be input into a third machine learning model 60 that outputs the target load threshold. In some embodiments, the bone geometry may be input into the third machine learning model 60 which then outputs the target load threshold.

FIGS. 2-8 illustrates one or more embodiments of an osteogenic, isometric exercise and rehabilitation assembly. An aspect of the disclosure includes an isometric exercise and rehabilitation assembly 100. The assembly 100 can include a frame 102. The assembly can further include one or more pairs of load handles 104, 106, 108 (e.g., three shown) supported by the frame 102. Each load handle in one of the pairs of load handles 104, 106, 108 can be symmetrically spaced from each other relative to a vertical plane of the assembly 100. For example, the vertical plane can bisect the assembly 100 in a longitudinal direction.

During exercise, a user can grip and apply force to one of the pairs of load handles 104, 106, 108. The term "apply force" can include a single force, more than one force, a range of forces, etc. and may be used interchangeably with "addition of load". Each load handle in the pairs of load handles 104, 106, 108 can include at least one load cell 110 for separately and independently measuring a force applied to, or a load added onto, respective load handles. Further, each foot plate 118 (e.g., a left foot plate and a right foot plate) can include at least one load cell 110 for separately and independently measuring a force applied to, or a load added onto, respective foot plates.

The placement of a load cell 110 in each pair of load handles 104, 106, 108 and/or feet plates 118 can provide the ability to read variations in force applied between the left and right sides of the user. This allows a user or trainer to understand relative strength. This is also useful in understanding strength when recovering from an injury.

In some embodiments, the assembly further can include the computing device 12. One or more of the load cells 110 can be individually in electrical communication with the computing device 12 either via a wired or wireless connection. In some embodiments, the user interface 18 presented via a display of the computing device 12 may indicate how to perform an exercise, how much load is being added, a target load threshold to be exceeded, historical information for the user about how much load was added at prior sessions, comparisons to averages, etc., as well as additional information, recommendations, notifications, and/or indications described herein.

In some embodiments, the assembly further includes a seat 112 supported by the frame 102 in which a user sits while applying force to the load handles and/or feet plates. In some embodiments, the seat 112 can include a support such as a backboard 114. In some embodiments, the position of the seat 112 is adjustable in a horizontal and/or vertical dimension. In some embodiments, the angle of the seat 112 is adjustable. In some embodiments, the angle of the backboard 114 is adjustable. Examples of how adjustments to the seat 112 and backboard 112 can be implemented include, but are not limited to, using telescoping tubes and pins, hydraulic pistons, electric motors, etc. In some embodiments, the seat 112 can further include a fastening system 116 (FIG. 7), such as a seat belt, for securing the user to the seat 112.

In one example, the seat 112 can include a base 113 that is slidably mounted to a horizontal rail 111 of the frame 102. The seat 112 can be selectively repositionable and secured as indicated by the double-headed arrow. In another example, the seat 112 can include one or more supports 117 (e.g., two shown) that are slidably mounted to a substantially vertical rail 115 of the frame 102. The seat 112 can be selectively repositionable and secured as indicated by the double-headed arrow.

In some embodiments, a pair of feet plate 118 can be located angled toward and in front of the seat 112. The user can apply force to the feet plate 118 (FIG. 5) while sitting in the seat 112 during a leg-press-style exercise. The leg-press-style exercise can provide or enable osteogenesis, bone growth or bone density improvement for a portion of the skeletal system of the user. Further, the leg-press-style exercise can provide or enable muscular hypertrophy for one or more muscles of the user. In a leg-press-style exercise, the user can sit in the seat 112, place their feet on respective feet plates 118, and push on the pair of feet plate 118 using their legs.

In some embodiments, adjustments can be made to the position of the pair of feet plate 118. For example, these adjustments can include the height of the pair of feet plate 118, the distance between the pair of feet plate 118 and the seat 112, the distance between each handle of the pair of feet plate 118, the angle of the pair of feet plate 118 relative to the user, etc. In some embodiments, to account for natural differences in limb length or injuries, each foot plate of the pair of feet plate 118 can be adjusted separately.

In some embodiments, a first pair of load handles 104 can be located above and in front of the seat 112. The user can apply force to the load handles 104 (FIG. 7) while being constrained in the seat 112 by the fastening system 116 in a core-pull-style exercise. The core-pull-style exercise can provide or enable osteogenesis, bone growth or bone density improvement for a portion of the skeletal system of the user. Further, the core-pull-style exercise can provide or enable muscular hypertrophy for one or more muscles of the user. In a core-pull-style exercise, while the lower body of the user is restrained from upward movement by the fastening system 116, the user can sit in the seat 112, apply the fastening system 116, hold the first pair of load handles 104, and pull on the first pair of load handles 104 using their arms.

In some embodiments, adjustments can be made to the position of the first pair of load handles 104. For example, these adjustments can include the height of the first pair of load handles 104, the distance between the first pair of load handles 104 and the seat 112, the distance between each handle of the first pair of load handles 104, the angle of the first load handles 104 relative to the user, etc. In some embodiments, to account for natural differences in limb length or injuries, each handle of the first pair of load handles 104 can be adjusted separately.

In one example, the first pair of load handles 104 can include a sub-frame 103 that is slidably mounted to a vertical rail 105 of the frame 102. The first pair of load handles 104 can be selectively repositionable and secured as indicated by the double-headed arrow.

In some embodiments, a second pair of load handles 106 can be spaced apart from and in the front of the seat 112. While seated (FIG. 6), the user can apply force to the second pair of load handles 106 in a chest-press-style exercise. The chest-press-style exercise can provide or enable osteogenesis, bone growth or bone density improvement for another portion of the skeletal system of the user. Further, the chest-press-style exercise can provide or enable muscular hypertrophy for one or more muscles of the user. In a chest-press-style exercise, the user can sit in the seat 112, hold the second pair of load handles 106, and push against the second pair of load handles 106 with their arms.

In some embodiments, adjustments can be made to the position of the second pair of load handles 106. These adjustments can include the height of the second pair of load handles 106, the distance between the second pair of load handles 106 and the seat 112, the distance between each handle of the second pair of load handles 106, the angle of the second load handles 106 relative to the user, etc. In some embodiments, to account for natural differences in limb length or injuries, each handle of the second pair of load handles 106 can be adjusted separately.

In one example, the second pair of load handles 106 can include the sub-frame 103 that is slidably mounted to the vertical rail 105 of the frame 102. The sub-frame 103 can be the same sub-frame 103 provided for the first pair of load handles 104, or a different, independent sub-frame. The second pair of load handles 106 can be selectively repositionable and secured as indicated by the double-headed arrow.

In some embodiments (FIG. 8), a third pair of load handles 108 can be located immediately adjacent the seat 112, such that the user can stand and apply force in a suitcase-lift-style exercise. The suitcase-lift-style exercise can provide or enable osteogenesis, bone growth or bone density improvement for still another portion of the skeletal system of the user. Further, the suitcase-lift-style exercise can provide or enable muscular hypertrophy for one or more muscles of the user. Examples of the third pair of load handles 108 can extend horizontally along a pair of respective axes that are parallel to the vertical plane. The third pair of load handles 108 can be horizontally co-planar, such that a user can apply force to them in a suitcase-lift-style exercise. In the suitcase-lift-style exercise, the user can stand on the floor or a horizontal portion of the frame 102, bend their knees, grip the third pair of load handles 108, and extend their legs to apply an upward force to the third pair of load handles 108.

In some embodiments, adjustments can be made to the position of the third pair of load handles 108. These adjustments can include the height of the third pair of load handles 108, the distance between the third pair of load handles 108 and the seat 112, the distance between each handle of the third pair of load handles 108, the angle of the third load handles 108 relative to the user, etc. In some embodiments, to account for natural differences in limb length or injuries, each handle of the third pair of load handles 108 can be adjusted separately.

In one example, each load handle 108 of the third pair of load handles 108 can include a sub-frame 109 that is slidably mounted in or to a vertical tube 107 of the frame 102. Each load handle 108 of the third pair of load handles 108 can be selectively repositionable and secured as indicated by the double-headed arrows.

In other embodiments (not shown), the third pair of load handles 108 can be reconfigured to be coaxial and located horizontally in front of the user along an axis that is perpendicular to the vertical plane. The user can apply force to the third pair of load handles 108 in a deadlift-style exercise. Like the suitcase-lift-style exercise, the deadlift-style exercise can provide or enable osteogenesis, bone growth or bone density improvement for a portion of the skeletal system of the user. Further, the deadlift-style exercise can provide or enable muscular hypertrophy for one or more muscles of the user. In the deadlift-style exercise, the user can stand on the floor or a horizontal portion of the frame 102, bend their knees, hold the third pair of load handles 108 in front of them, and extend their legs to apply an upward force to the third pair of load handles 108. In some embodiments, the third pair of load handles 108 can be adjusted (e.g., rotated) from the described coaxial position used for the deadlift-style exercise, to the parallel position (FIGS. 7, 8) used for the suitcase lift-style exercise. The third pair of load handles 108, or others, can be used in a grip strengthening-style exercise to improve strength in the muscles of the hand and forearm.

Figure 9:
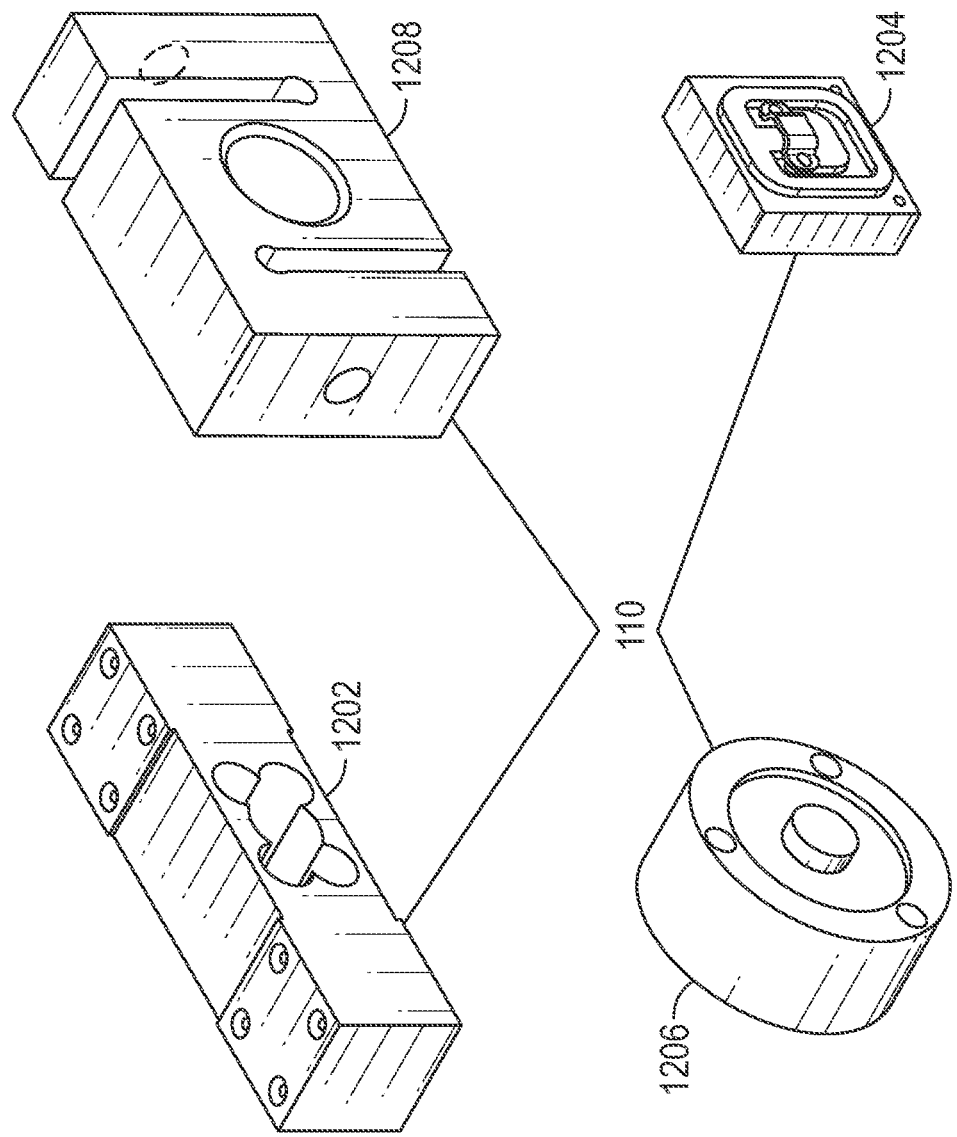
FIG. 9 illustrates four examples of load cells that can be used in the isometric exercise assembly.

FIG. 9 depicts several options for the load cells 110. In some embodiments, the load cells 110 can be piezoelectric load cells, such as PACEline CLP Piezoelectric Subminiature Load Washers. In other embodiments, the load cells 110 can be hydraulic load cells, such as NOSHOK hydraulic load cells. In some versions, the load cells 110 can include strain gauges. Embodiments of the strain gauges can be bending-type strain gauges, such as Omega SGN-4/20-PN 4 mm grid, 20 ohm nickel foil resistors. Other examples of the strain gauges can be double-bending-type strain gauges 1202, such as Rudera Sensor RSL 642 strain gauges. Still other embodiments of the strain gauges can be half-bridge-type strain gauges 1204, such as Onyehn 4pcs 50 kg Human Scale Load Cell Resistance Half-bridge/Amplifier Strain Weight Sensors with 1pcs HX711 AD Weight Modules for Arduino DIY Electronic Scale strain gauges. In some embodiments, the strain gauges can be S-type strain gauges 1206, such as SENSORTRONICS S-TYPE LOAD CELL 60001 strain gauges. Additionally, the strain gauges can be button-type strain gauges 1208, such as Omega LCGB-250 250 lb Capacity Load Cells. Naturally, the load cells 110 can comprise combinations of these various examples. The embodiments described herein are not limited to these examples.

Figure 10:
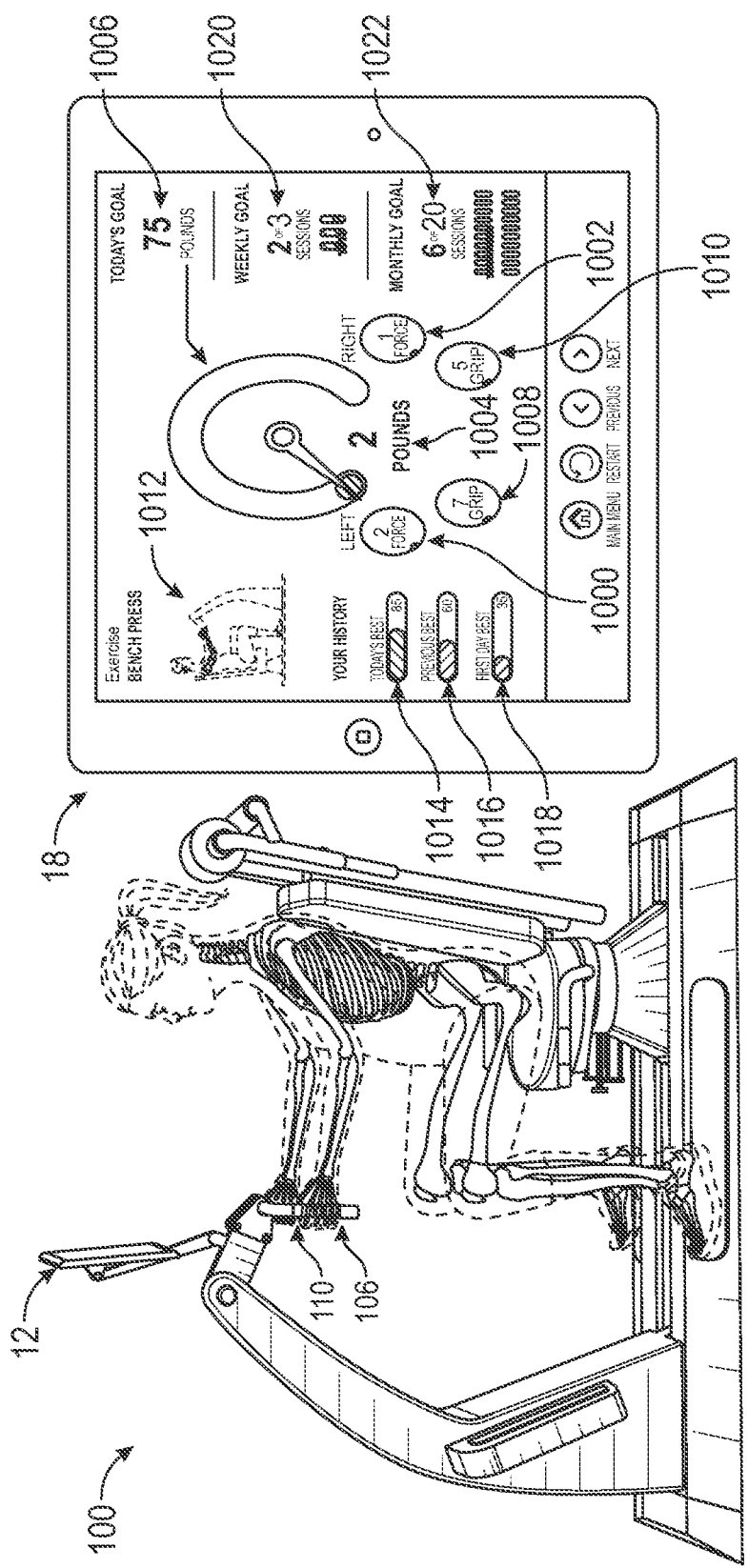
FIG. 10 illustrates a side view of a second embodiment of the isometric exercise and rehabilitation assembly with the user performing a chest-press-style exercise and a user interface presenting information to the user.

FIG. 10-13 illustrate views of a second embodiment of the isometric exercise and rehabilitation assembly 100. FIG. 10 illustrates a side view of the second embodiment of the isometric exercise and rehabilitation assembly 100 with the user performing a chest-press-style exercise and a user interface 18 presenting information to the user. As depicted, the user is the gripping second pair of load handles 106. A left load cell 110 and a right load cell 110 may be located at a left load handle 106 and a right load handle 106, respectively, in the second pair of load handles 106. The user may push on the second pair of load handles 106 to add load to the left load cell 110 and the right load cell 110. The left load cell 110 may transmit a left load measurement to the computing device 102, and the right load cell 110 may transmit a right load measurement to the computing device 102. The computing device 102 may use the load measurements to provide various real-time feedback on the user interface 18 as the user performs the chest-press-style exercise.

In general, the user interface 18 may present real-time visual feedback of the current load measurements or the current forces corresponding to the load measurements, a weight in pounds associated with the load measurements, target load thresholds, and indications when the target load thresholds are exceeded. The control system may provide various visual, audio, and/or haptic feedback when the user exceeds their target load thresholds.

As depicted, the user interface 18 presents a left load measurement 1000 as a left force and a right load measurement 1002 as a right force in real-time or near real-time as the user is pressing on the second pair of handles 106. The values of the forces for the left load measurement 1000 and the right load measurement 1002 are presented. There are separate visual representations for the left load measurement 1000 and the right load measurement 1002. In some embodiments, these load measurements 1000 and 1002 may be represented in a bar char, line chart, graph, or any suitable visual representation. In some embodiments, a left target load threshold and a right target load threshold for the user may be presented on the user interface 18. In some embodiments, the left and right target load thresholds may be different. For example, if the user fractured their left arm and is rehabilitating the left arm, but the user's right arm is healthy, the left target load threshold may be different from the right target load threshold.

If the left load measurement 1000 exceeds the left target load threshold, an indication (e.g., starburst) may be presented on the user interface 18 indicating that the left target load threshold has been exceeded and/or osteogenesis has been triggered in one or more portions of the body. If the right load measurement 1002 exceeds the right target load threshold, an indication (e.g., starburst) may be presented on the user interface 18 indicating that the right target load threshold has been exceeded and/or osteogenesis has been triggered in another portion of the body. Further, if either or both of the left and right target load thresholds are exceeded, the indication may indicate that the exercise is complete and a congratulatory message may be presented on the user interface 18.

In some embodiments, there may be a single target load threshold to which both the left load measurement and the right load measurement are compared. If either of the left or right load measurement exceed the single target load threshold, the above-described indication may be presented on the user interface 18.

In some embodiments, more than one target limit may be used. For example, if the bone geometry and/or bone density of a left leg differs from a bone geometry and/or bone density of a right leg, then different target load thresholds may be determined for the left and right leg.

Further, a total weight 1004 in pounds that is determined based on the left and right load measurements is presented on the user interface 18. The total weight 1004 may dynamically change as the user adds load onto the load cells 110. A target weight 1006 for the exercise for the current day is also presented. This target weight 1006 may be determined based on the user's historical performance for the exercise. If the total weight 1004 exceeds the target weight 1006, an indication (e.g., starburst) may be presented on the user interface 18 indicating that osteogenesis and/or muscular hypertrophy has been triggered. Further, the indication may indicate that the exercise is complete and a congratulatory message may be presented on the user interface 18. In some embodiments, another message may be presented on the user interface 18 that encourages the user to continue adding load to set a new personal maximum record for the exercise.

Additionally, the user interface 18 may present a left grip strength 1008 and a right grip strength 1010. In some embodiments, the left grip strength and the right grip strength may be determined based on the left load measurement and the right load measurement, respectively. Numerical values representing the left grip strength 1008 and the right grip strength 1010 are displayed. Any suitable visual representation may be used to present the grip strengths (e.g., bar chart, line chart, etc.). The grip strengths may only be presented when the user is performing an exercise using handles.

The user interface 18 may also present a prompt 1012 that indicates the body position the user should be in to perform the exercise, as well as indicate which body portions will be targeted by performing the exercise. The user interface 18 may present other current and historical information related to the user performing the particular exercise. For example, the user interface 18 may present a visual representation 1014 of the user's maximum weight lifted, pressed, pulled, or otherwise exerted force for the day or a current exercise session. The user interface 18 may present a visual representation 1016 of the user's previous maximum weight lifted, pressed, pulled, or otherwise exerted force. The user interface 18 may present a visual representation 1018 of the user's maximum weight lifted, pressed, pulled, or otherwise exerted force the first time the user performed the exercise. The user interface 18 may present one or more visual representations 1020 for a weekly goal including how many sessions should be performed in the week and progress of the sessions as they are being performed. The user interface 18 may present a monthly goal including how many sessions should be performed in the month and progress of the sessions as they are being performed. Additional information and/or indications (e.g., incentivizing messages, recommendations, warnings, congratulatory messages, etc.) may be presented on the user interface 18, as discussed further below.

Figure 11:
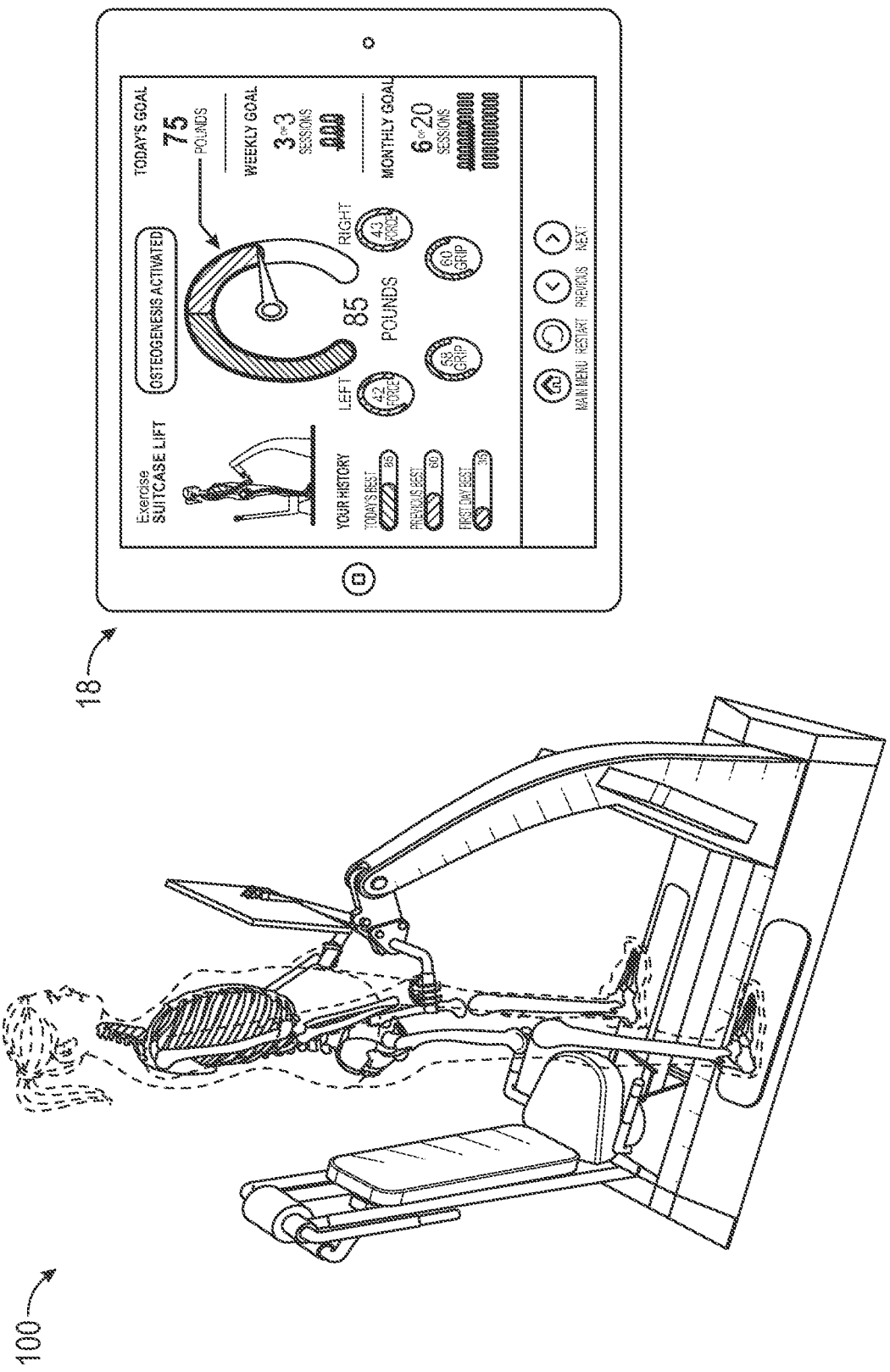
FIG. 11 illustrates a side view of the second embodiment of the isometric exercise and rehabilitation assembly with a user performing a suitcase-lift-style exercise and a user interface presenting information to the user.

FIG. 11 illustrates a side view of the second embodiment of the isometric exercise and rehabilitation assembly 100 with a user performing a suitcase-lift-style exercise and the user interface 18 presenting information to the user. The user interface 18 may present similar types of information as discussed above with regards to FIG. 10, but the information in the user interface 18 in FIG. 11 may be tailored for the suit-case-lift-style exercise.

Figure 12:
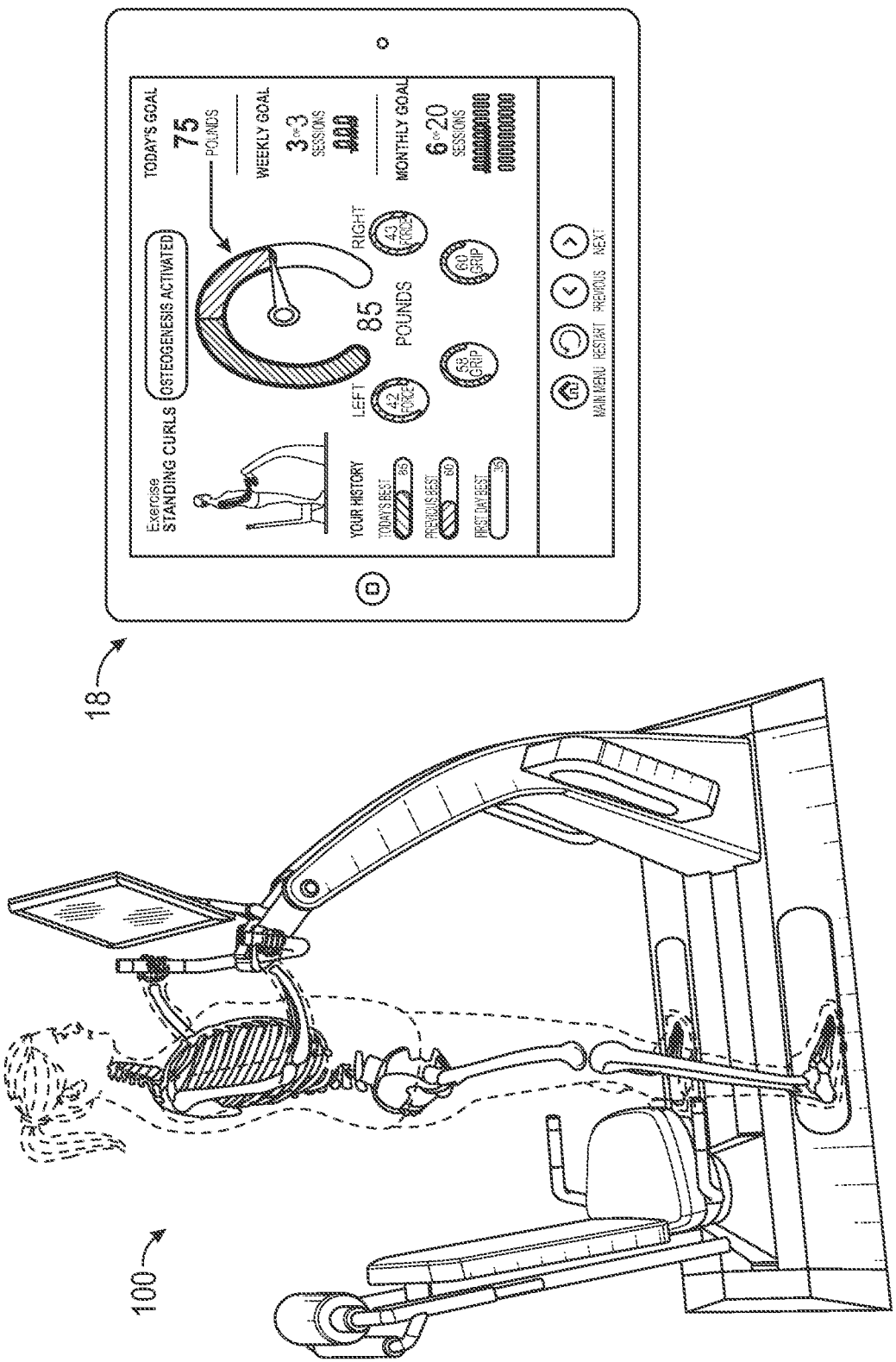
FIG. 12 illustrates a side view of the second embodiment of the isometric exercise and rehabilitation assembly with a user performing an arm-curl-style exercise and a user interface presenting information to the user.

FIG. 12 illustrates a side view of the second embodiment of the isometric exercise and rehabilitation assembly 100 with a user performing an arm-curl-style exercise and a user interface presenting information to the user. The user interface 18 may present similar types information as discussed above with regards to FIG. 10, but the information in the user interface 18 in FIG. 12 may be tailored for the arm-curl-style exercise.

FIG. 13 illustrates a side view of the second embodiment of the isometric exercise and rehabilitation assembly 100 with a user performing a leg-press-style exercise and a user interface presenting information to the user. The user interface 18 may present similar types information as discussed above with regards to FIG. 10, but the information in the user interface 18 in FIG. 13 may be tailored for the leg-press-style exercise.

Figure 14:
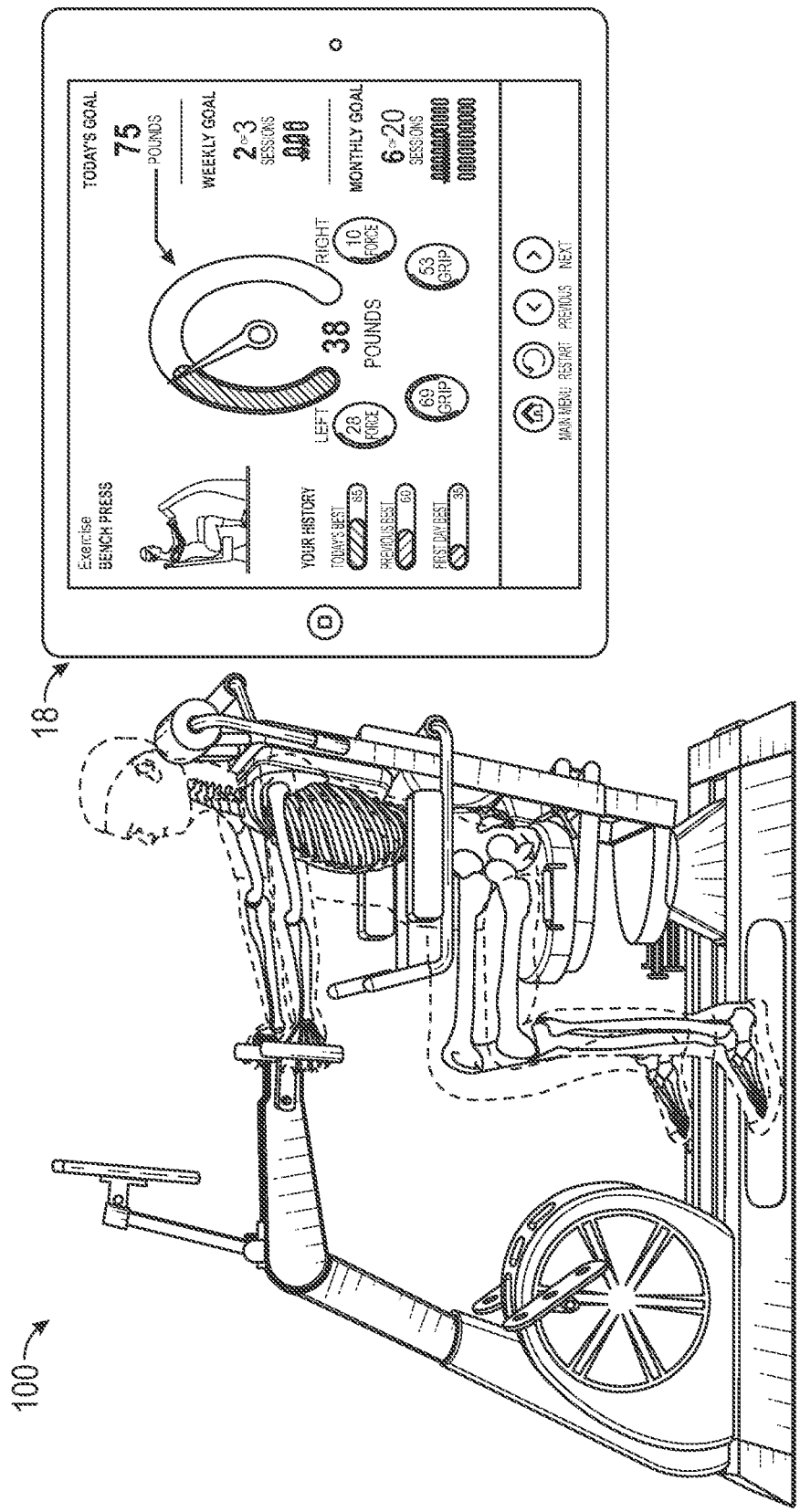
FIG. 14 illustrates a side view of a third embodiment of the isometric exercise and rehabilitation assembly with the user performing a chest-press-style exercise and a user interface presenting information to the user.

FIGS. 14-18 illustrate views of a third embodiment of the isometric exercise and rehabilitation assembly 100. FIG. 14 illustrates a side view of the third embodiment of the isometric exercise and rehabilitation assembly 100 with the user performing a chest-press-style exercise and a user interface 18 presenting information to the user. The user interface 18 in FIG. 14 may present similar types of information as discussed above with regards to FIG. 10.

Figure 15:
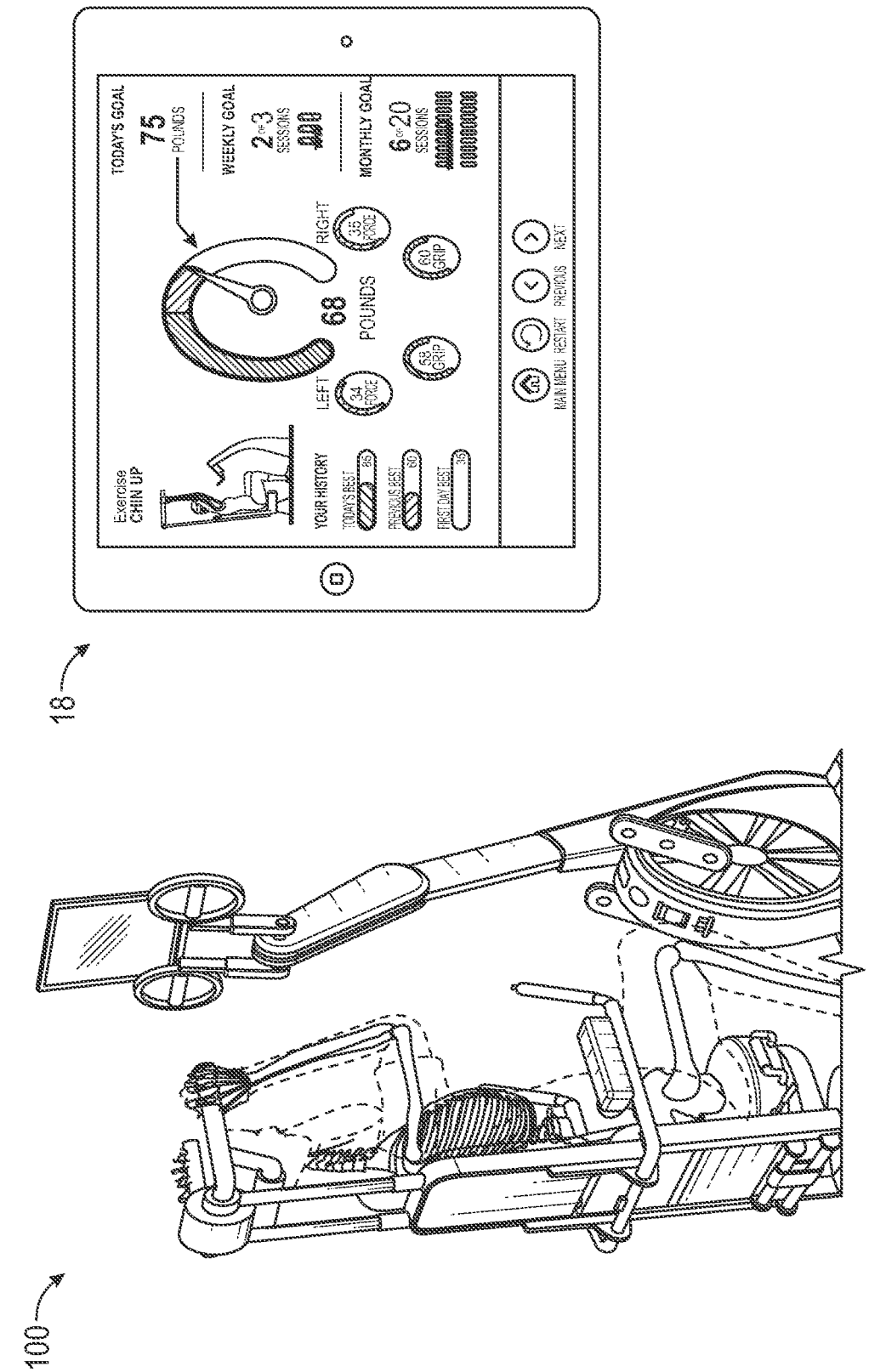
FIG. 15 illustrates a side view of the third embodiment of the isometric exercise and rehabilitation assembly with the user performing a pull-down-style exercise and a user interface presenting information to the user.

FIG. 15 illustrates a side view of the third embodiment of the isometric exercise and rehabilitation assembly 100 with the user performing a pull-down-style exercise and a user interface 18 presenting information to the user. The user interface 18 may present similar types of information as discussed above with regards to FIG. 10, but the information in the user interface 18 in FIG. 15 may be tailored for the pull-down-style exercise.

Figure 16:
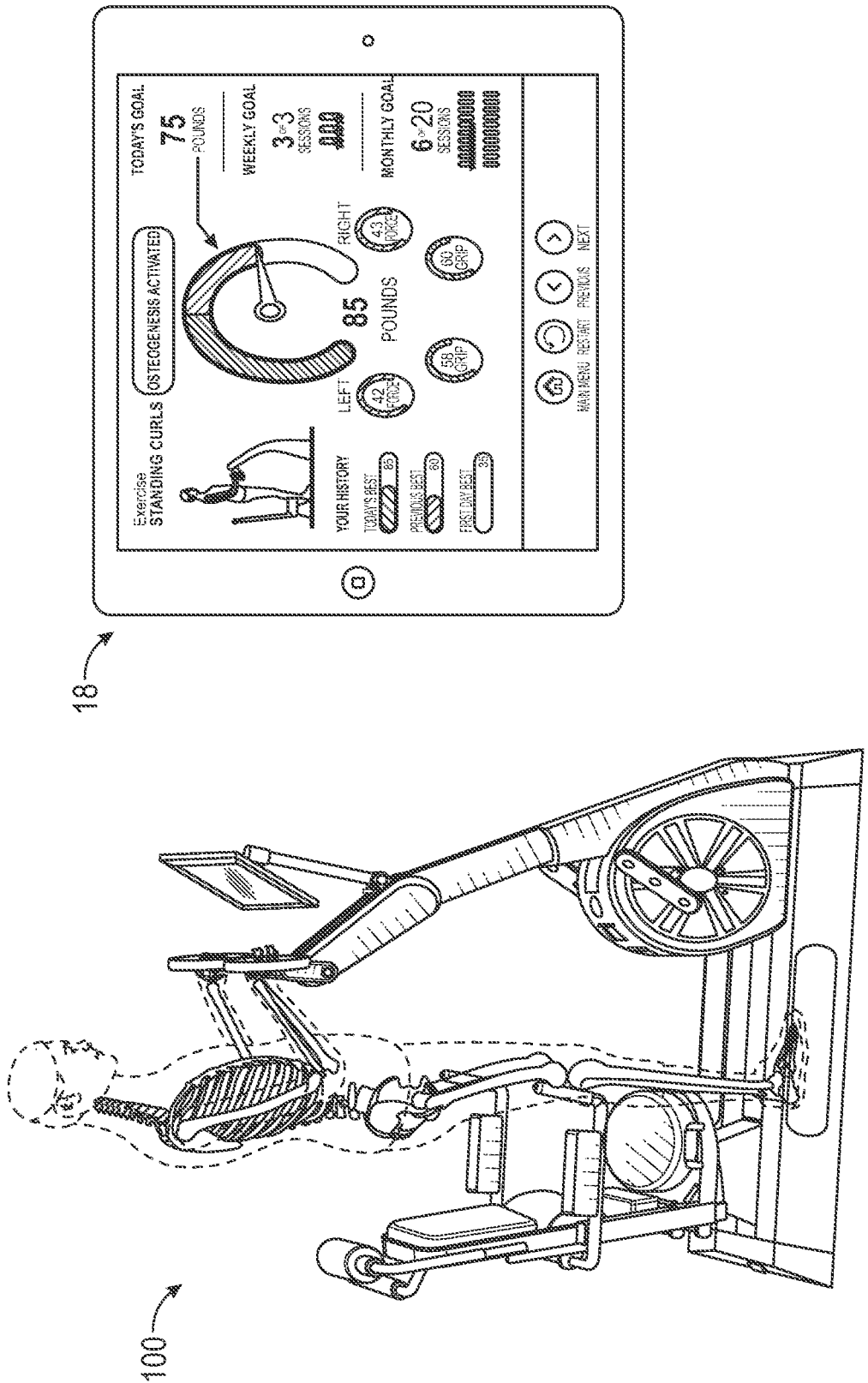
FIG. 16 illustrates a side view of the third embodiment of the isometric exercise and rehabilitation assembly with a user performing an arm-curl-style exercise and a user interface presenting information to the user.

FIG. 16 illustrates a side view of the third embodiment of the isometric exercise and rehabilitation assembly with a user performing an arm-curl-style exercise and a user interface 18 presenting information to the user. The user interface 18 may present similar types of information as discussed above with regards to FIG. 12.

Figure 17:
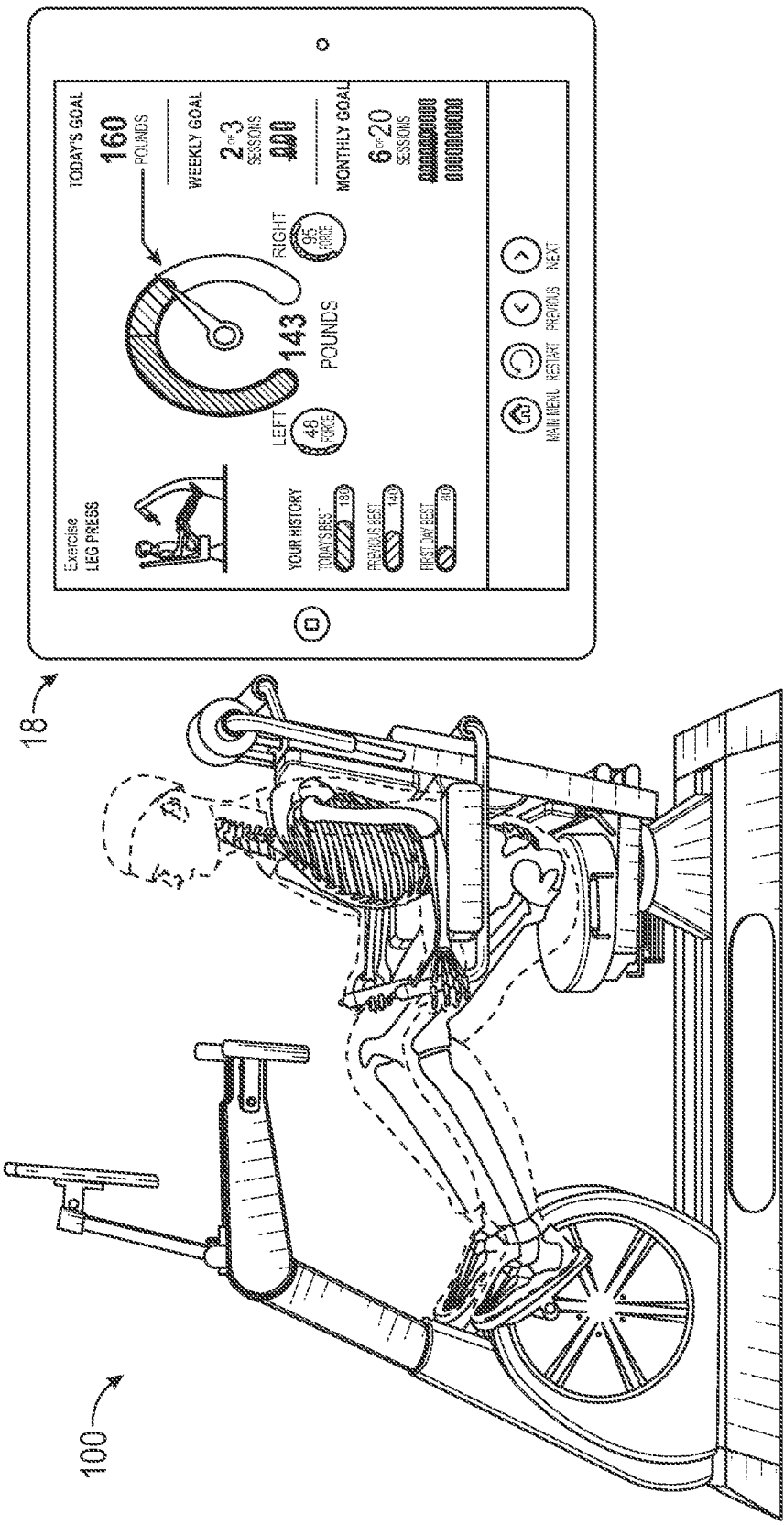
FIG. 17 illustrates a side view of the third embodiment of the isometric exercise and rehabilitation assembly with a user performing a leg-press-style exercise and a user interface presenting information to the user.

FIG. 17 illustrates a side view of the third embodiment of the isometric exercise and rehabilitation assembly 100 with a user performing a leg-press-style exercise and a user interface 18 presenting information to the user. The user interface 18 may present similar types of information as discussed above with regards to FIG. 13.

Figure 18:
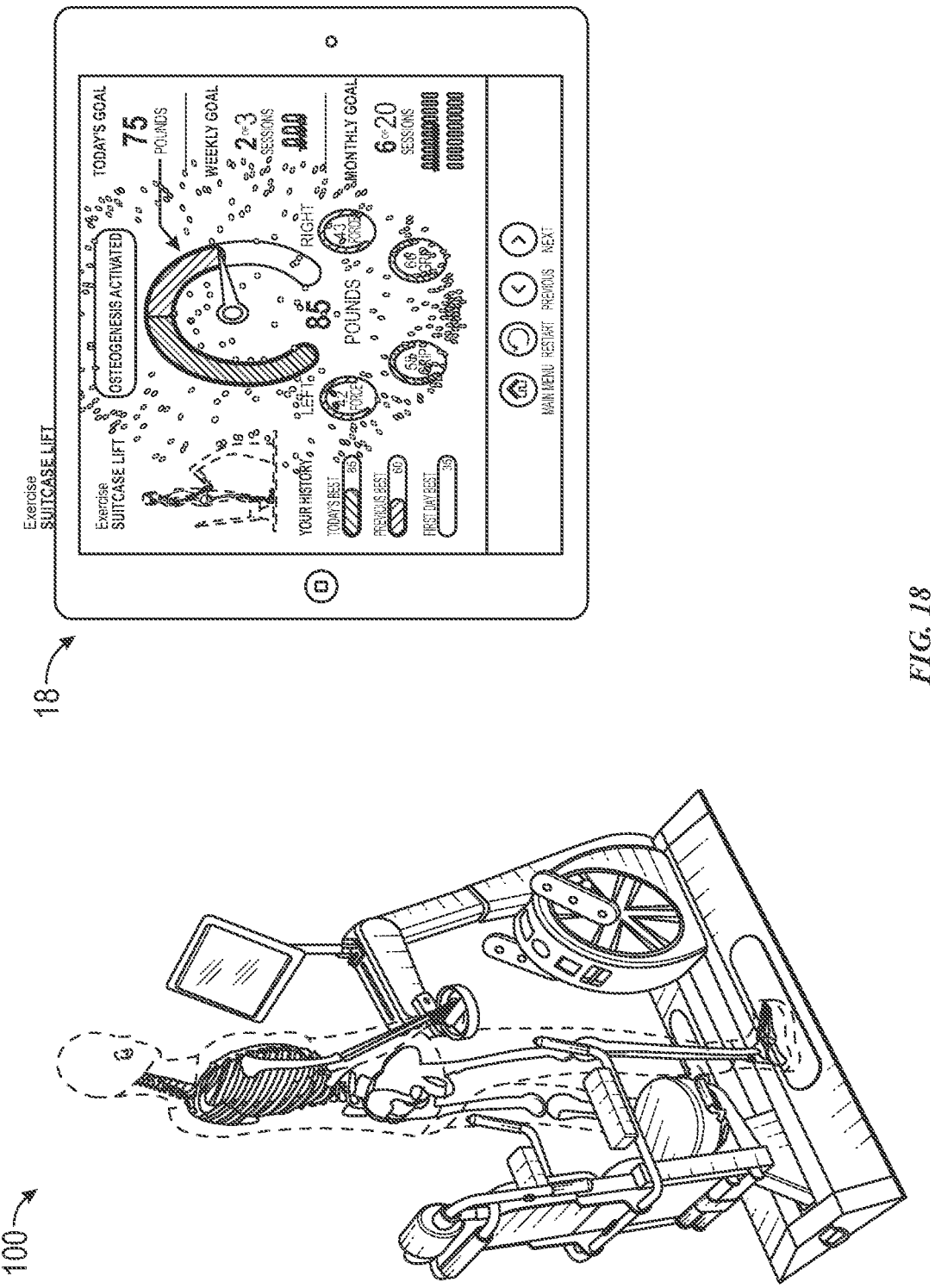
FIG. 18 illustrates a side view of the third embodiment of the isometric exercise and rehabilitation assembly with a user performing a suitcase-lift-style exercise and a user interface presenting information to the user.

FIG. 18 illustrates a side view of the third embodiment of the isometric exercise and rehabilitation assembly 100 with a user performing a suitcase-lift-style exercise and a user interface 18 presenting information to the user. The user interface 18 may present similar types of information as discussed above with regards to FIG. 11.

Figure 19:
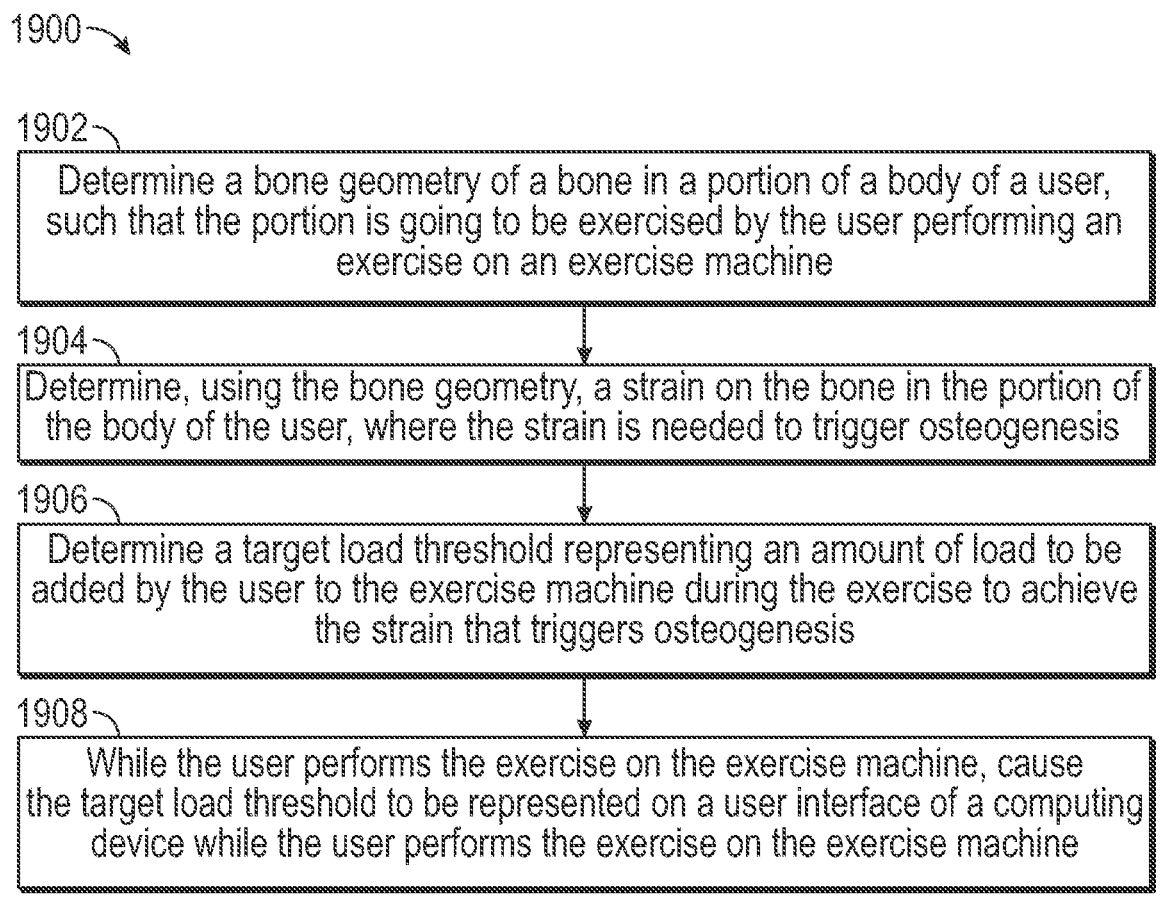
FIG. 19 illustrates example operations of a method for intelligent self-calibration of thresholds for users using an exercise machine.

FIG. 19 illustrates example operations of a method 1900 for intelligent self-calibration of thresholds for users using an exercise machine. The method 1900 may be performed by processing logic that may include hardware (circuitry, dedicated logic, etc.), firmware, software, or a combination of them. The method 1900 and/or each of their individual functions, subroutines, or operations may be performed by one or more processing devices of a control system (e.g., computing device 12 of FIG. 1) implementing the method 1900. The method 1900 may be implemented as computer instructions executable by a processing device of the control system. In certain implementations, the method 1900 may be performed by a single processing thread. Alternatively, the method 1900 may be performed by two or more processing threads, each thread implementing one or more individual functions, routines, subroutines, or operations of the methods. Various operations of the method 1900 may be performed by one or more of the cloud-based computing system 16, and/or the computing device 15 of FIG. 1.

At 1902, the processing device may determine a bone geometry of a bone in a portion of a body, such that the portion is going to be exercised by the user performing an exercise on an exercise machine 100. The bone geometry of the bone may be determined for the left side, the right side, or both sides of the user. For example, if the user is engaged in a leg-press-style exercise, the bone geometry of one or more bones in the left leg may be determined, and the bone geometry of one or more bones in the right leg may be determined. Methods 2000, 2010, and/or 2020 in FIGS. 20A, 20B, and/or 20C, respectively, describe further details about determining the bone geometry in 1902.

Returning to the method 1900 in FIG. 19, at 1904, the processing device may determine, using the bone geometry, a strain on the bone in the portion of the body of the user, where the degree of the strain is needed to trigger osteogenesis. In some embodiments, the strain may be determined for desired bones in the left side, the right side, or both sides of the user. In some embodiments, determining the strain on the bone in the portion of the body of the user needed to trigger osteogenesis may include using the bone geometry and empirical data. The empirical data may include at least one of (i) first empirical data of changes to the bone geometry of the user caused by strains on the bone that result from the user applying loads on an exercise machine while performing the exercise or a series of the exercise over time, or (ii) second empirical data of changes caused by a set of strains that result from the set of users applying a set of loads while performing the exercise or series of the exercise over time to a set of bone geometries of a set of bones of a set of users.

The first empirical data may represent historical performance of the user applying loads to the exercise machine 100 during a series of exercises over time and a correlation between the applied loads and the changes of bone geometry over time. The first empirical data may include a maximum amount of load the user has applied to one or more load cells 110 associated with each exercise of the exercise machine 100. The first empirical data may include a grip strength of the user. The first empirical data may be correlated with other data pertaining to the user, such as height, weight, age, gender, race, etc. Such first empirical data may be used to determine one or more target load thresholds that the user is to exceed to cause sufficient strain on a bone to trigger osteogenesis. For example, as the bone geometry of the user changes over time, the first empirical data may be used to determine target load thresholds for a series of one or more exercises performed by the user.

In some embodiments, the first empirical data may be obtained for each user of the exercise machine 110 and the first empirical data may be fit to a respective curve for each respective user. The strain needed to trigger osteogenesis for each bone geometry of the respective users may be represented on the respective curves. The curves may be compared and used to identify another user's bone geometry, such that it is similar to the bone geometry of the current user of the exercise machine 100 and such that the strain that triggers osteogenesis for the bone geometry of the current user based on the strain that triggers osteogenesis in the identified bone geometry of the other user may be identified. The first empirical data may be used as training data to train a machine learning model 60 to output a strain based on any of the first empirical data being input into the machine learning model 60.

The second empirical data may represent population data and/or a clinical study of users and changes to bone geometries (e.g., determined by performing bone density scans) of the users that result from the strains caused by applications of loads during a series of exercises (e.g., leg presses, arm curls, etc.) over time. The second empirical data may include a particular multiple of body weight identified as triggering osteogenesis in respective bones in the human body and the multiple of body weight may be used as a baseline when, using the bone geometry, the strain is determined.

In some embodiments, the second empirical data may be fit to a curve. The strain needed to trigger osteogenesis for each bone geometry of the users may be represented on the curve. As such, the curve may be used to identify the bone geometry similar to the bone geometry of the current user of the exercise machine 100 and to identify the strain that triggers osteogenesis for the identified bone geometry. In some embodiments, other data sources (e.g., height, weight, body mass index, applied loads, multiples of body weight) may be correlated with the strain and the bone geometries and fit on the curve, as well. Fitting data to the curve may produce an equation that may be used to calculate, based on an input bone geometry, a strain. Such second empirical data may be used to determine one or more target load thresholds that the user is to exceed to cause sufficient strain on a bone to trigger osteogenesis. For example, the second empirical data may be used to determine target load thresholds for a series of one or more exercises performed by the user as the bone geometry of the user changes over time.

The second empirical data may be used as training data to train a machine learning model 60 to output a strain based on any of the second empirical data being input into the machine learning model 60. In some embodiments, if a direct correlation of an application of a certain axial load that causes osteogenesis to a certain bone geometry is identified, the strain may not be determined and the certain axial load can be used as a target load threshold for that certain determined bone geometry of the user. Method 2100 in FIGS. 21A-21B describes further details pertaining to how the strain may be determined in 1904.

In some embodiments, the first empirical data and the second empirical data may be combined and fit to a multi-dimensional curve that may be used, based on bone geometries of the user at any given time when the user performs the exercise, to determine strain and/or target load thresholds. The first empirical and the second empirical data may be used as training data to train a machine learning model 60 to output a strain and/or a target load threshold based on any of the first empirical data and/or the second empirical data being input into the machine learning model 60.

Returning to the method 1900 in FIG. 19, at 1906, the processing device may determine a target load threshold representing an amount of load to be added by the user to the exercise machine 100 during the exercise, in order to achieve the strain that triggers osteogenesis. In some embodiments, the target load threshold may be determined for the left side, the right side, or both sides of the user. Accordingly, one or more target load thresholds may be determined. Method 2200 in FIG. 22 describes further details pertaining to how the target load threshold may be determined in 1906.

Returning to the method 1900 in FIG. 19, at 1908, while the user performs the exercise on the exercise machine 100, the processing device may cause the target load threshold to be represented on the user interface 18 of the computing device 12. The target load threshold may be presented in response to the processing device detecting that the user is starting the exercise. In some embodiments, the processing device may determine that the user is starting an exercise by detecting a minimum threshold load being applied to a load cell 110 associated with the exercise.

The processing device may receive a load measurement from the load cell 110 associated with the exercise. In some embodiments, the processing device may receive a left load measurement from a load cell 110 at a left portion of the exercise machine 110 and a right load measurement from a load cell 110 at a right portion of the exercise machine 100. The processing device may determine whether the load measurement exceeds the target load threshold. In some embodiments, the processing device may determine whether the left load measurement exceeds a left target load threshold for a left portion of the body of the user and whether the right load measurement exceeds a right target load threshold for a right portion of the body of the user. Responsive to determining that the one or more load measurements exceeds the one or more target load thresholds, the processing device may be configured to cause the user interface 18 to present an indication that the one or more target load thresholds have been exceeded and osteogenesis has been triggered in the applicable portion (e.g., left and/or right) of the body.

In some embodiments, the processing device may, based on changes to the bone geometry of the user, modify the target load threshold. Each time the user performs the exercise, the bone geometry of the user may be determined. If the bone geometry decreases or is the same as a previously determined bone geometry, the target load threshold may be adjusted (e.g., increased). If the bone geometry changes (e.g., the bone density increases) between exercises, then the target load threshold may increase to achieve the sufficient strain to trigger osteogenesis in the changed bone geometry.

For example, the processing device may determine a second bone geometry of the bone in the portion of the body of the user that is going to be exercised by the user performing a second exercise on the exercise machine 100. The second exercise may be of the same type (e.g., leg-press-style, arm-curl-style, etc.) as the exercise previously performed by the user. The processing device may determine, using the bone geometry, a second strain on the bone needed to trigger osteogenesis in the portion of the body of the user. The processing device may determine a second target load threshold to be added by the user to the exercise machine during the second exercise, in order to achieve the strain that triggers osteogenesis for the second bone geometry. While the user performs the exercise on the exercise machine 100, the second target load threshold may be presented on the user interface 18 of the computing device 12.

Accordingly, the disclose embodiments may enable intelligent self-calibration of target load thresholds that may optimize triggering osteogenesis for users, thereby increasing bone growth more efficiently. Further, the disclosed techniques may provide a better experience for the user using the computing system 12 because the user interface 18 presents the target load thresholds tailored for the individual user and indications when osteogenesis is triggered.

Figure 20A:
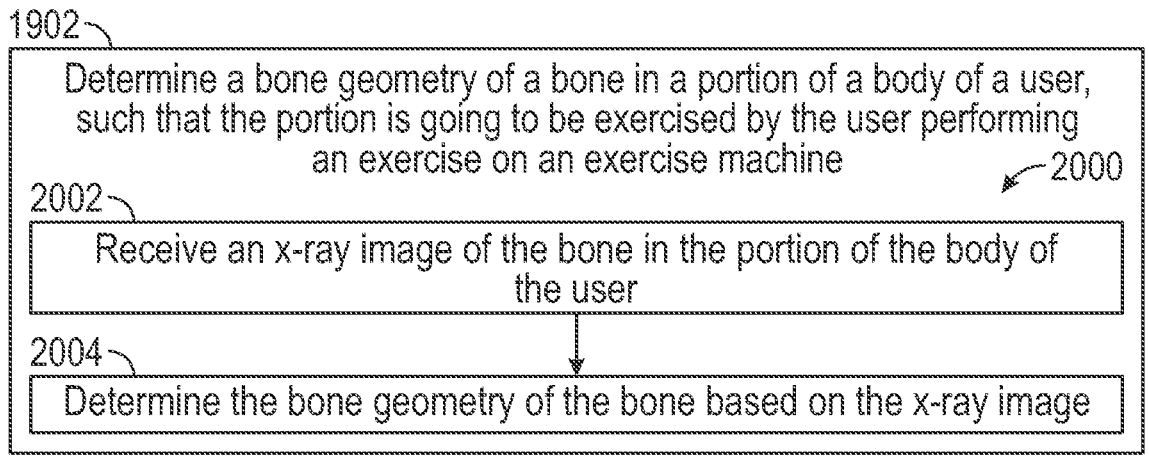
FIGS. 20A-20C illustrate example operations of methods for determining bone geometry
Figure 20B:
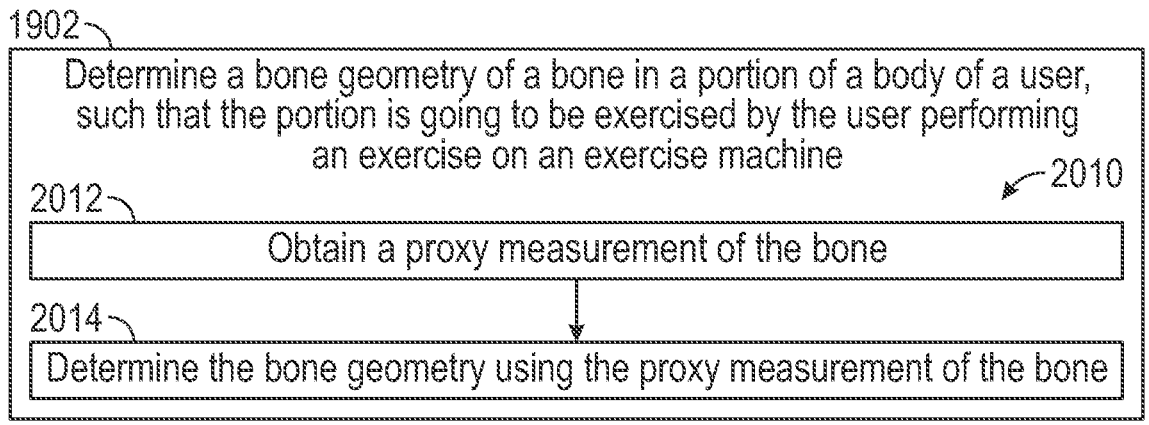
Figure 20C:
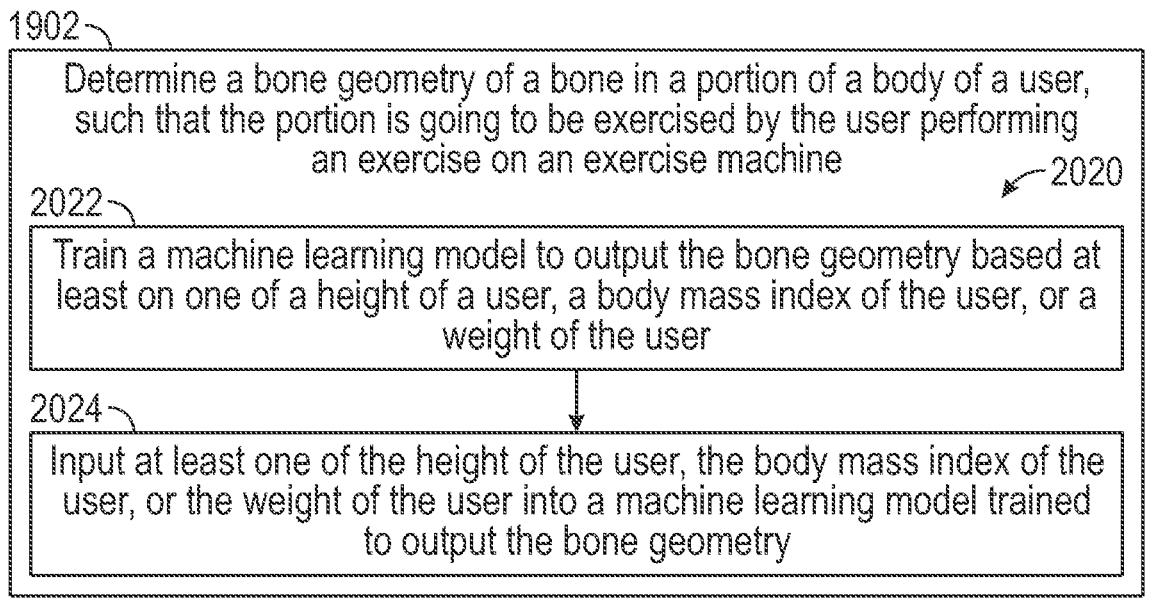

FIGS. 20A-20C illustrate example operations of methods 2000, 2010, and 2020 for determining bone geometry (1902 in the method 1900 of FIG. 19). Methods 2000, 2010, and 2020 include operations performed by processing devices of the control system (e.g., computing device 12) of FIG. 1. In some embodiments, one or more operations of the methods 2000, 2010, and 2020 are implemented in computer instructions executable by a processing device of the control system. Various operations of the methods 2000, 2010, and 2020 may be performed by one or more of the computing device 15 and/or the cloud-based computing system 16. In regard to method 1900, the methods 2000, 2010, and 2020 may be performed in the same or a similar manner as described above.

Beginning with the method 2000 in FIG. 20A, at 2002, the processing device may receive an X-ray image of the bone in the portion of the body of the user. The X-ray image may be a digital image and may be received by the computing device 12 from an X-ray device communicatively coupled (e.g., via the network 20) to the computing device 12.

At 2004, the processing device may determine the bone geometry of the bone of based on the X-ray image. For example, the processing device may be configured to perform object character recognition to identify the bone in the X-ray image. In some embodiments, color values of pixels of the X-ray image may be analyzed to identify the bone. The processing device may be configured to perform measurements of the bone to determine the bone geometry.

Turning to the method 2010 in FIG. 20B, at 2012, the processing device may obtain a proxy measurement of the bone. A proxy measurement may include obtaining the bone geometry without performing an X-ray on the portion of the body that includes the bone. For example, a proxy measurement may include measuring a diameter of the portion of the body and/or a length of the portion of the body. The measurement may be manually entered using the computing device 12, retrieved from memory of the computing device 12, received from the cloud-based computing system 16 or the computing device 15, or received from a measuring device communicatively coupled to the computing device 12.

At 2014, the processing device may determine the bone geometry using the proxy measurement. For example, the computing device 12 may store correlations between the proxy measurements and bone geometries generated from historical data. In some embodiments, the processing device may use the correlations to determine the bone geometry for the obtained proxy measurements.

Turning to the method 2020 in FIG. 20C, at 2022, the processing device may train a machine learning model 60 to output the bone geometry based at least on one of a height of a user, a body mass index of the user, or a weight of the user. Empirical data obtained from clinical studies, for example, may be used to train the machine learning model 60. The empirical data may be correlated with other training data when training the machine learning model 60. The other training data may include heights, body mass indices, and/or weights of users and their bone geometries for each bone in their body.

At 2024, the processing device may input at least one of the height of the user, the body mass index of the user, or the weight of the user into the machine learning model 60 trained to output the bone geometry. The bone geometry may be used to determine the strain and/or the target load threshold required to trigger osteogenesis in the bone in the portion of the body being exercised.

Figure 21:
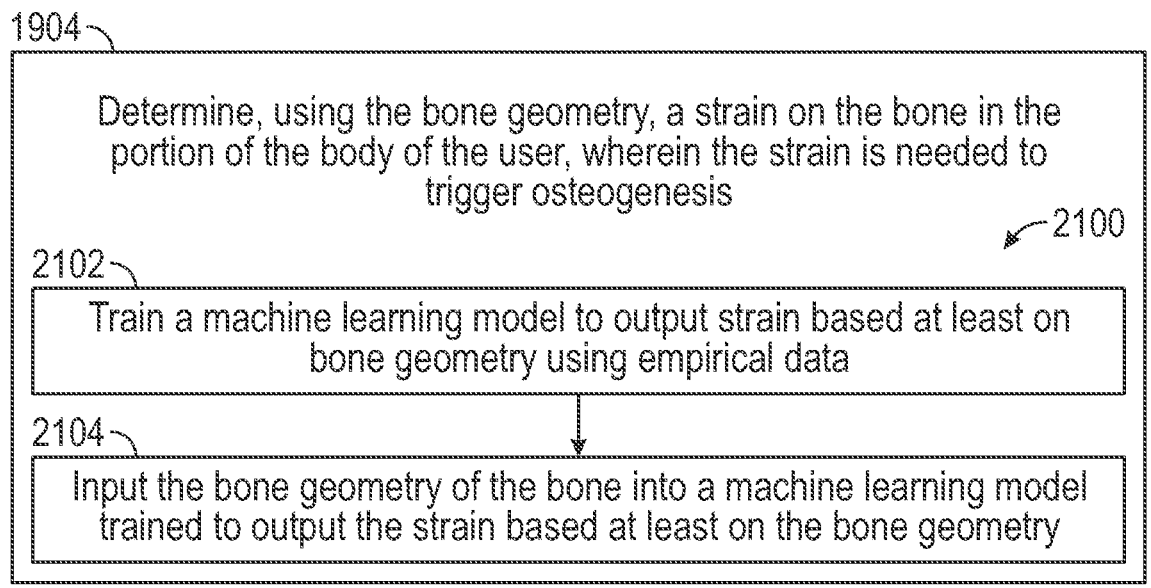
FIG. 21 illustrates example operations of a method for determining, using the bone geometry, a strain on the bone in a portion of a body of a user to trigger osteogenesis.

FIG. 21 illustrates example operations of a method 2100 for determining, using the bone geometry, a strain on the bone in a portion of a body of a user to trigger osteogenesis (1904 in the method 1900 of FIG. 19). Method 2100 includes operations performed by processing devices of the control system (e.g., computing device 12) of FIG. 1. In some embodiments, one or more operations of the method 2100 are implemented in computer instructions executable by a processing device of the control system. Various operations of the method 2100 may be performed by one or more of the computing device 15 and/or the cloud-based computing system 16. In regard to method 1900, the method 2100 may be performed in the same or a similar manner as described above.

At 2102, the processing device may train a machine learning model 60 to output strain using empirical data based at least on bone geometry. In some embodiments, the empirical data may include tracked changes to bone geometries of users, where the changes are caused by strains that result from the users applying loads while performing the exercise. Such empirical data may correlate the different bone geometries over time with the loads applied that results in the strain on the bone causing the changes. Further, the empirical data may include one or more multiples of body weight identified through research, and further identified as triggering osteogenesis in one or more bones of the user. The empirical data may be correlated with one or more other data and/or factors, such as heights of the users, weights of the users, body mass indices of the users, ages of the users, genders of the users, health conditions of the users, races of the users, etc.

At 2104, based at least on the bone geometry, the processing device may input the bone geometry of the bone of the user performing the exercise on the exercise machine 100 into the machine learning model 60 trained to output the strain. In some embodiments, the strain may be used to determine the target load threshold that the user is to exceed to trigger osteogenesis.

FIGS. 22A-22B illustrate example operations of methods 2200 and 2210 for determining a target load threshold to be added by the user to the exercise machine 100 during the exercise to achieve the strain that triggers osteogenesis (1906 in the method 1900 of FIG. 19). Methods 2200 and 2210 include operations performed by processing devices of the control system (e.g., computing device 12) of FIG. 1. In some embodiments, one or more operations of the methods 2200 and 2210 are implemented in computer instructions executable by a processing device of the control system. Various operations of the methods 2200 and 2210 may be performed by one or more of the computing device 15 and/or the cloud-based computing system 16. In regard to method 190, the methods 2200 and 2210 may be performed in the same or a similar manner as described above.

Beginning with the method 2200 in FIG. 22A, at 2202, the processing device may simulate, using a mathematical model of the physical bone, such a mathematical model having the bone geometry, one or more axial loads on the bone having the bone geometry. The physical mathematical model may implement a finite element method that finds partial differential equation solutions to boundary value problems. The physical mathematical model may model the bone and amounts of strain experienced at points on the bone in response to the application of the one or more axial loads.

At 2204, when the axial load causes the strain on the bone in the portion of the body of the user that triggers osteogenesis, the processing device may select an axial load as the target load threshold. That is, during the simulations, when an axial load is identified that causes the strain determined in 1904 of method 1900 in FIG. 19, the processing device may select that axial load as the target load threshold to be exceeded by the user to at least the extent needed to trigger osteogenesis.

Turning to the method 2210 in FIG. 22B, at 2202, the processing device may train a machine learning model 60 to output the target load threshold based at least on bone geometry using at least empirical data. In some embodiments, the empirical data may pertain to tracked changes to bone geometries of bones of users, where the changes are caused by strains that result from the users applying loads while performing the exercise. Such empirical data may correlate the different bone geometries over time with the strains triggering osteogenesis resulting in the respective different bone geometries. In some embodiments, a direct correlation may be identified between a certain applied load and the bone geometries that causes osteogenesis in bones having certain bone geometries. Further, the empirical data may include one or more multiples of body weight identified through research, where such multiples are identified as triggering osteogenesis in one or more bones of the user. The empirical data may be correlated with one or more other data and/or factors, such as heights of the users, weights of the users, body mass indices of the users, ages of the users, genders of the users, races of the users, etc.

At 2214, the processing device may input the bone geometry of the bone of the user performing the exercise on the exercise machine 100 into the machine learning model 60 trained, based at least on the bone geometry, to output the target load threshold. The target load threshold may be presented on the user interface 18 of the computing device 12.

Figure 23:
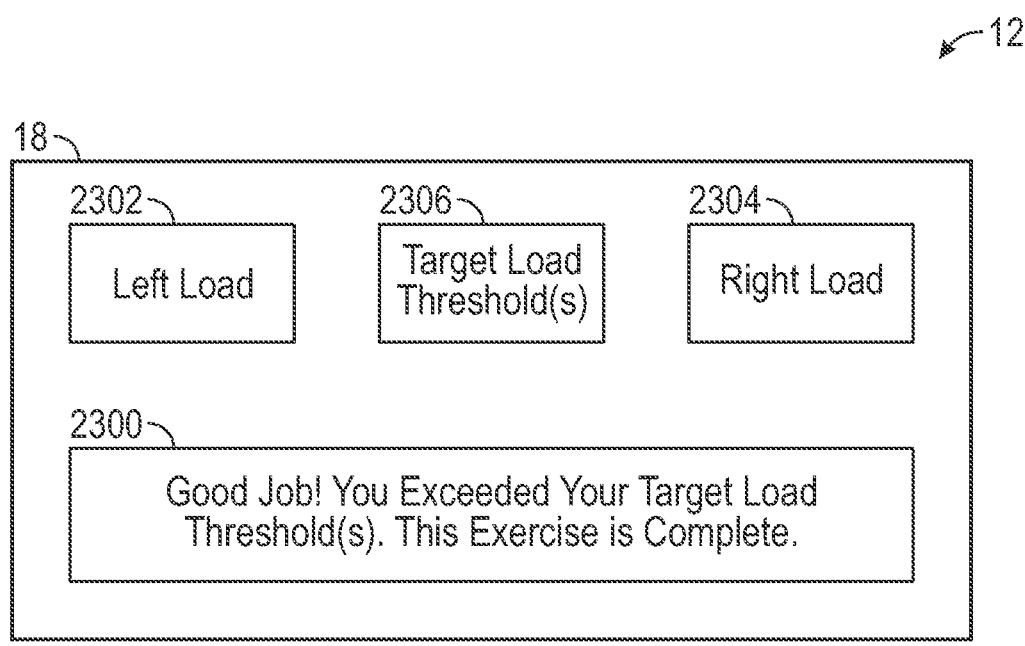
FIG. 23 illustrates an example user interface presenting an indication that one or more target load thresholds have been exceeded.

FIG. 23 illustrates an example user interface 18 presenting an indication 2300 that an exercise is complete, resulting in the user's being congratulated. For example, the indication 2300 states: "Good job! You exceeded your target load threshold(s). This exercise is complete." The user interface 18 may present visual representations 2302 and/or 2304 for the left and right load measurements, respectively. In some embodiments, the visual representations 2202 and/or 2204 may be numerical values representing the respective load measurements. In some embodiments, the visual representation 2202 and/or 2204 may be bars on a bar chart, lines on a line chart, or any suitable visual representation.

Further, the user interface 18 may present one or more visual representations 2206 of target load thresholds tailored for the user. For example, the one or more target load thresholds may include a left target load threshold, a right target load threshold, or some combination thereof. Presenting the visual representations 2206 of the target load thresholds concurrently with the real-time display of the load measurements in the visual representations 2202 and/or 2204 may enable the user to determine how close they are to exceeding the target load thresholds and/or when they exceed the target load thresholds.

Figure 24:
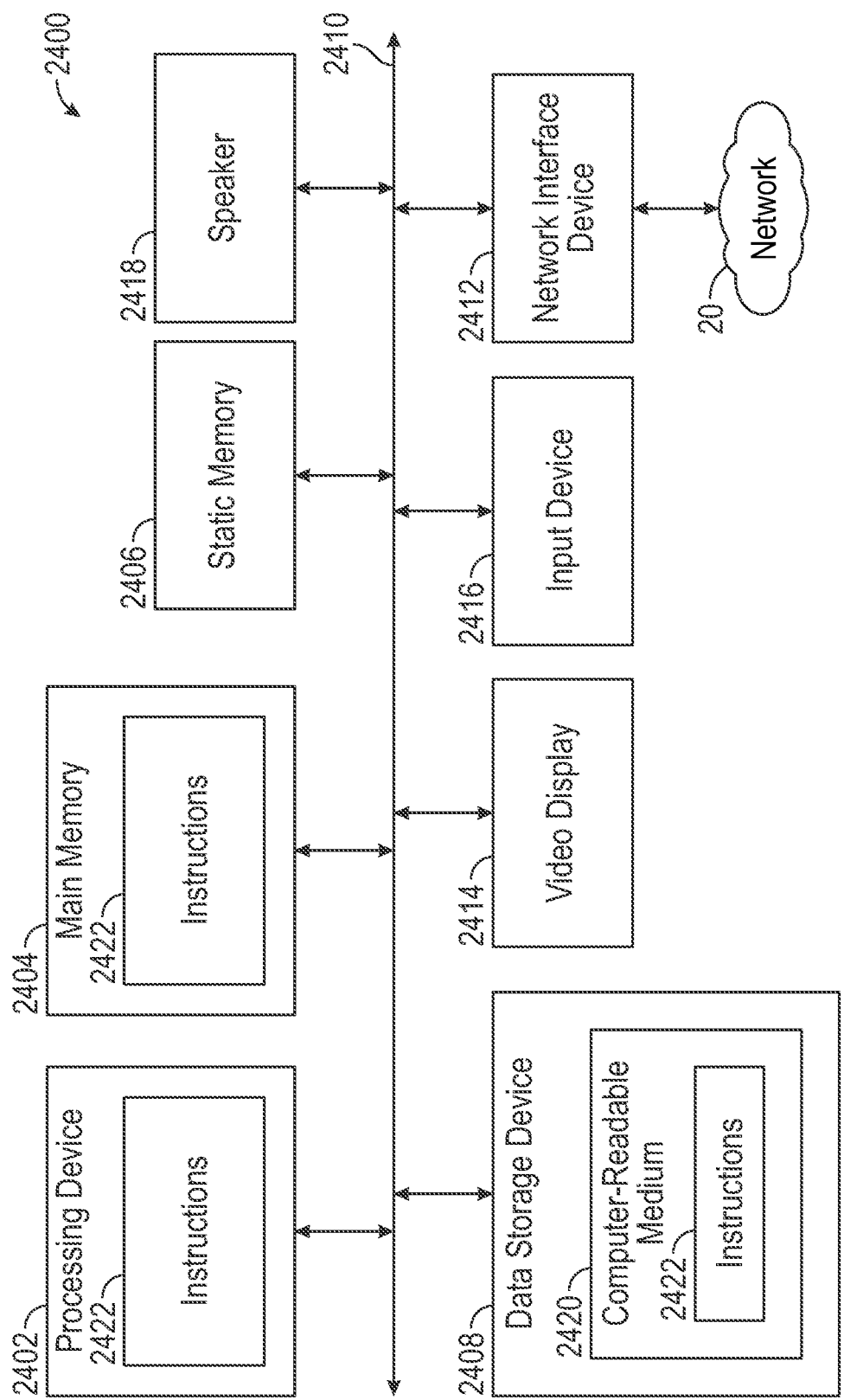
FIG. 24 illustrates an example computer system.

FIG. 24 illustrates an example computer system 2400, which can perform any one or more of the methods described herein. In one example, computer system 2400 may correspond to the computing device 12 (e.g., control system), the computing device 15, one or more servers 28 of the cloud-based computing system 16, or one or more training engines 50 of the cloud-based computing system 16 of FIG. 1. The computer system 2400 may be capable of executing the application 17 and presenting the user interface 18 of FIG. 1, and/or the application 21 and presenting the user interface 22 of FIG. 1. The computer system 2400 may be connected (e.g., networked) to other computer systems in a LAN, an intranet, an extranet, or the Internet. The computer system 2400 may operate in the capacity of a server in a client-server network environment. The computer system 2400 may be a personal computer (PC), a tablet computer, a wearable (e.g., wristband), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 2400 includes a processing device 2402, a main memory 2404 (e.g., read-only memory (ROM), solid state drive (SSD), flash memory, dynamic random access memory (DRAM) such as synchronous DRAM (SDRAM)), a static memory 2406 (e.g., solid state drive (SSD), flash memory, static random access memory (SRAM)), and a data storage device 2408, which communicate with each other via a bus 2410.

Processing device 2402 represents one or more general-purpose processing devices such as a microprocessor, central processing unit, or the like. More particularly, the processing device 2402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 2402 may also be one or more special-purpose processing devices such as an application specific integrated circuit (ASIC), a field programmable gate array (FPGA), a digital signal processor (DSP), network processor, or the like. The processing device 2402 is configured to execute instructions for performing any of the operations and steps discussed herein.

The computer system 2400 may further include a network interface device 2412. The computer system 2400 also may include a video display 2414 (e.g., a liquid crystal display (LCD) or a cathode ray tube (CRT)), one or more input devices 2416 (e.g., a keyboard and/or a mouse), and one or more speakers 2418 (e.g., a speaker). In one illustrative example, the video display 2414 and the input device(s) 2416 may be combined into a single component or device (e.g., an LCD touch screen).

The data storage device 2416 may include a computer-readable medium 2420 on which the instructions 2422 (e.g., implementing the application 17 or 21 executed by any device and/or component depicted in the FIGURES and described herein) embodying any one or more of the methodologies or functions described herein are stored. The instructions 2422 may also reside, completely or at least partially, within the main memory 2404 and/or within the processing device 2402 during execution thereof by the computer system 2400. As such, the main memory 2404 and the processing device 2402 also constitute computer-readable media. The instructions 2422 may further be transmitted or received over a network via the network interface device 2412.

While the computer-readable storage medium 2420 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The various aspects, embodiments, implementations or features of the described embodiments can be used separately or in any combination. The embodiments disclosed herein are modular in nature and can be used in conjunction with or coupled to other embodiments, including both statically-based and dynamically-based equipment. In addition, the embodiments disclosed herein can employ selected equipment such that they can identify individual users and auto-calibrate threshold multiple-of-body-weight targets, as well as other individualized parameters, for individual users.

1. A method, comprising:
determining, by one or more processing devices, a bone geometry of a bone in a portion of a body of a user, such that the portion is going to be exercised by the user performing an exercise on an exercise machine;
determining, using the bone geometry, a strain on the bone in the portion of the body of the user, wherein the strain is needed to trigger osteogenesis;
determining a target load threshold representing an amount of load to be added by the user to the exercise machine during the exercise to achieve the strain that triggers osteogenesis; and
while the user performs the exercise on the exercise machine, causing the target load threshold to be represented on a user interface of a computing device.

2. The method of claim 1, further comprising modifying the target load threshold based on changes to the bone geometry of the user.

3. The method of claim 1, further comprising:
determining, by the one or more processing devices, a second bone geometry of the bone in the portion of the body of the user, such that the portion is going to be exercised by the user performing a second exercise on the exercise machine, wherein the exercise and the second exercise are of a same type;
determining, using the bone geometry, a second strain on the bone in the portion of the body of the user, wherein the strain is needed to trigger osteogenesis; and
determining a second target load threshold representing a second amount of load to be added during the second exercise by the user to the exercise machine to achieve the strain that triggers osteogenesis.

4. The method of claim 1, wherein determining, using the bone geometry, the strain on the bone in the portion of the body of the user, wherein the strain needed to trigger osteogenesis further comprises:
inputting the bone geometry of the bone into a machine learning model trained to output, based at least on the bone geometry, the strain.

5. The method of claim 4, further comprising training, based at least on the bone geometry using empirical data that tracks changes to a plurality of bone geometries of a plurality of bones of a plurality of users, wherein the changes are caused by a plurality of strains that result from the plurality of users applying a plurality of loads while performing the exercise, the machine learning model to output the strain.

6. The method of claim 1, wherein determining, using the bone geometry, the strain on the bone in the portion of the body of the user, wherein the strain needed to trigger osteogenesis further comprises:
determining, using the bone geometry and empirical data, the strain on the bone, wherein the empirical data comprises at least one of:
a set of first empirical data of changes to the bone geometry of the user, wherein the changes are caused by strains on the bone that result from the user applying loads while performing the exercise, or
a set of second empirical data of changes to a plurality of bone geometries of a plurality of bones of a plurality of users, wherein the changes are caused by a plurality of strains that result from the plurality of users applying a plurality of loads while performing the exercise.

7. The method of claim 1, further comprising using empirical data of similar bone geometries of a plurality of bones of a plurality of users and loads applied to those similar bone geometries, such that strains occur which are sufficient to trigger osteogenesis in the plurality of bones.

8. The method of claim 1, wherein determining the bone geometry of the bone in the portion of the body of the user further comprises:
receiving an X-ray image of the bone in the portion of the body of the user; and
based on the X-ray image, determining the bone geometry of the bone.

9. The method of claim 1, wherein determining the bone geometry of the bone in the portion of the body of the user further comprises:
obtaining a proxy measurement of the bone, wherein the proxy measurement comprises obtaining the bone geometry without performing an X-ray; and
using the proxy measurement of the bone, determining the bone geometry.

10. The method of claim 9, wherein obtaining the bone geometry without performing an X-ray further comprises at least one of obtaining a measurement of a diameter of the portion of the body or a length of the portion of the body.

11. The method of claim 1, wherein determining the bone geometry of the bone in the portion of the body of the user further comprises:
inputting at least one of a height of the user, a body mass index of the user, or a weight of the user into a machine learning model trained to output, based on at least one of the height of the user, the body mass index of the user, or the weight of the user, the bone geometry.

12. The method of claim 1, further comprising:
receiving a load measurement from a load cell of the exercise machine;
determining whether the load measurement exceeds the target load threshold; and
responsive to determining that the load measurement exceeds the target load threshold, causing the user interface to present an indication that the target load threshold has been exceeded.

13. The method of claim 1, wherein determining the target load threshold representing an amount of load to be added by the user to the exercise machine to achieve the strain that triggers osteogenesis further comprises:
simulating, using a mathematical model of the bone having the bone geometry, one or more axial loads on the bone having the bone geometry; and
selecting an axial load as the target load threshold when the axial load causes the strain on the bone in the portion of the body of the user that triggers osteogenesis.

14. The method of claim 1, wherein the bone geometry comprises a bone density, a bone dimension, a bone length, a bone diameter, or some combination thereof.

15. A tangible, non-transitory computer-readable medium storing instructions that, when executed by a processing device, cause the processing device to:
  determine a bone geometry of a bone in a portion of a body of a user, such that the portion is going to be exercised by the user performing an exercise on an exercise machine;
  determine, using the bone geometry, a strain on the bone in the portion of the body of the user, wherein the strain is needed to trigger osteogenesis;
  determine a target load threshold representing an amount of load to be added by the user to the exercise machine during the exercise to achieve the strain that triggers osteogenesis; and
  while the user performs the exercise on the exercise machine, cause the target load threshold to be represented on a user interface of a computing device.

16. The tangible, non-transitory computer-readable medium of claim 15, wherein the processing device is further configured to modify the target load threshold based on changes to the bone geometry of the user.

17. The tangible, non-transitory computer-readable medium of claim 15, wherein the processing device is further configured to:
  simulate, using a mathematical model of the bone having the bone geometry, one or more axial loads on the bone having the bone geometry; and
  select an axial load as the target load threshold when the axial load causes the strain on the bone in the portion of the body of the user that triggers osteogenesis.

18. The tangible, non-transitory computer-readable medium of claim 15, wherein, to determine the bone geometry of the bone in the portion of the body of the user, the processing device is further configured to:
  receive an X-ray image of the bone in the portion of the body of the user; and
  based on the X-ray image, determine the bone geometry of the bone.

19. The tangible, non-transitory computer-readable medium of claim 15, wherein the processing device is further to use empirical data of similar bone geometries of a plurality of bones of a plurality of users and loads applied to those similar bone geometries, such that strains occur which are sufficient to trigger osteogenesis in the plurality of bones.

20. A system, comprising:
  one or more memory devices storing instructions; and
  one or more processing devices communicatively coupled to the one or more memory devices, wherein the one or more processing devices are configured to execute the instructions to:
    determine a bone geometry of a bone in a portion of a body of a user that is going to be exercised by the user, such that the portion is performing an exercise on an exercise machine;
    determine, using the bone geometry, a strain on the bone in the portion of the body of the user, wherein the strain is needed to trigger osteogenesis;
    determine a target load threshold representing an amount of load to be added by the user to the exercise machine during the exercise to achieve the strain that triggers osteogenesis; and
    while the user performs the exercise on the exercise machine, cause the target load threshold to be represented on a user interface of a computing device.

The foregoing description, for purposes of explanation, used specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The invention claimed is:
1. A method, comprising:
  determining, by one or more processing devices, a bone geometry of a bone in a portion of a body of a user, such that the portion is going to be exercised by the user performing an exercise on an exercise machine;
  determining, using the bone geometry, a strain on the bone in the portion of the body of the user, wherein the strain is needed to trigger osteogenesis;
  determining a target load threshold representing an amount of load to be added by the user to the exercise machine during the exercise to achieve the strain that triggers osteogenesis; and
  while the user performs the exercise on the exercise machine, causing the target load threshold to be represented on a user interface of a computing device.

2. The method of claim 1, further comprising modifying the target load threshold based on changes to the bone geometry of the user.

3. The method of claim 1, further comprising:
  determining, by the one or more processing devices, a second bone geometry of the bone in the portion of the body of the user, such that the portion is going to be exercised by the user performing a second exercise on the exercise machine, wherein the exercise and the second exercise are of a same type;
  determining, using the bone geometry, a second strain on the bone in the portion of the body of the user, wherein the strain is needed to trigger osteogenesis; and
  determining a second target load threshold representing a second amount of load to be added during the second exercise by the user to the exercise machine to achieve the strain that triggers osteogenesis.

4. The method of claim 1, wherein determining, using the bone geometry, the strain on the bone in the portion of the body of the user, wherein the strain needed to trigger osteogenesis further comprises:
  inputting the bone geometry of the bone into a machine learning model trained to output, based at least on the bone geometry, the strain.

5. The method of claim 4, further comprising training, based at least on the bone geometry using empirical data that tracks changes to a plurality of bone geometries of a plurality of bones of a plurality of users, wherein the changes are caused by a plurality of strains that result from the plurality of users applying a plurality of loads while performing the exercise, the machine learning model to output the strain.

6. The method of claim 1, wherein determining, using the bone geometry, the strain on the bone in the portion of the body of the user, wherein the strain needed to trigger osteogenesis further comprises:
  determining, using the bone geometry and empirical data, the strain on the bone, wherein the empirical data comprises at least one of:
    a set of first empirical data of changes to the bone geometry of the user, wherein the changes are caused by strains on the bone that result from the user applying loads while performing the exercise, or
    a set of second empirical data of changes to a plurality of bone geometries of a plurality of bones of a plurality of users, wherein the changes are caused by a plurality of strains that result from the plurality of users applying a plurality of loads while performing the exercise.

7. The method of claim 1, further comprising using empirical data of similar bone geometries of a plurality of bones of a plurality of users and loads applied to those similar bone geometries, such that strains occur which are sufficient to trigger osteogenesis in the plurality of bones.

8. The method of claim 1, wherein determining the bone geometry of the bone in the portion of the body of the user further comprises:
  receiving an X-ray image of the bone in the portion of the body of the user; and
  based on the X-ray image, determining the bone geometry of the bone.

9. The method of claim 1, wherein determining the bone geometry of the bone in the portion of the body of the user further comprises:
  obtaining a proxy measurement of the bone, wherein the proxy measurement comprises obtaining the bone geometry without performing an X-ray; and
  using the proxy measurement of the bone, determining the bone geometry.

10. The method of claim 9, wherein obtaining the bone geometry without performing an X-ray further comprises at least one of obtaining a measurement of a diameter of the portion of the body or a length of the portion of the body.

11. The method of claim 1, wherein determining the bone geometry of the bone in the portion of the body of the user further comprises:
  inputting at least one of a height of the user, a body mass index of the user, or a weight of the user into a machine learning model trained to output, based on at least one of the height of the user, the body mass index of the user, or the weight of the user, the bone geometry.

12. The method of claim 1, further comprising:
  receiving a load measurement from a load cell of the exercise machine;
  determining whether the load measurement exceeds the target load threshold; and
  responsive to determining that the load measurement exceeds the target load threshold, causing the user interface to present an indication that the target load threshold has been exceeded.

13. The method of claim 1, wherein determining the target load threshold representing an amount of load to be added by the user to the exercise machine to achieve the strain that triggers osteogenesis further comprises:
  simulating, using a mathematical model of the bone having the bone geometry, one or more axial loads on the bone having the bone geometry; and
  selecting an axial load as the target load threshold when the axial load causes the strain on the bone in the portion of the body of the user that triggers osteogenesis.

14. The method of claim 1, wherein the bone geometry comprises a bone density, a bone dimension, a bone length, a bone diameter, or some combination thereof.

15. A tangible, non-transitory computer-readable medium storing instructions that, when executed by a processing device, cause the processing device to:
  determine a bone geometry of a bone in a portion of a body of a user, such that the portion is going to be exercised by the user performing an exercise on an exercise machine;
  determine, using the bone geometry, a strain on the bone in the portion of the body of the user, wherein the strain is needed to trigger osteogenesis;
  determine a target load threshold representing an amount of load to be added by the user to the exercise machine during the exercise to achieve the strain that triggers osteogenesis; and
  while the user performs the exercise on the exercise machine, cause the target load threshold to be represented on a user interface of a computing device.

16. The tangible, non-transitory computer-readable medium of claim 15, wherein the processing device is further configured to modify the target load threshold based on changes to the bone geometry of the user.

17. The tangible, non-transitory computer-readable medium of claim 15, wherein the processing device is further configured to:
  simulate, using a mathematical model of the bone having the bone geometry, one or more axial loads on the bone having the bone geometry; and
  select an axial load as the target load threshold when the axial load causes the strain on the bone in the portion of the body of the user that triggers osteogenesis.

18. The tangible, non-transitory computer-readable medium of claim 15, wherein, to determine the bone geometry of the bone in the portion of the body of the user, the processing device is further configured to:
  receive an X-ray image of the bone in the portion of the body of the user; and
  based on the X-ray image, determine the bone geometry of the bone.

19. The tangible, non-transitory computer-readable medium of claim 15, wherein the processing device is further to use empirical data of similar bone geometries of a plurality of bones of a plurality of users and loads applied to those similar bone geometries, such that strains occur which are sufficient to trigger osteogenesis in the plurality of bones.

20. A system, comprising:
  one or more memory devices storing instructions; and
  one or more processing devices communicatively coupled to the one or more memory devices, wherein the one or more processing devices are configured to execute the instructions to:
    determine a bone geometry of a bone in a portion of a body of a user that is going to be exercised by the user, such that the portion is performing an exercise on an exercise machine;
    determine, using the bone geometry, a strain on the bone in the portion of the body of the user, wherein the strain is needed to trigger osteogenesis;
    determine a target load threshold representing an amount of load to be added by the user to the exercise machine during the exercise to achieve the strain that triggers osteogenesis; and while the user performs the exercise on the exercise machine, cause the target load threshold to be represented on a user interface of a computing device.

* * * * *